US012161398B2

(12) United States Patent
Chou et al.

(10) Patent No.: US 12,161,398 B2
(45) Date of Patent: *Dec. 10, 2024

(54) ULTRASOUND SEQUENCING METHOD

(71) Applicant: Acutus Medical, Inc., Carlsbad, CA (US)

(72) Inventors: Derrick R. Chou, San Diego, CA (US); Graydon E. Beatty, Bloomington, MN (US); Marcus Julian, Vista, CA (US); Timothy J. Corvi, Carlsbad, CA (US); J. Christopher Flaherty, Nottingham, NH (US); R. Maxwell Flaherty, Topsfield, MA (US)

(73) Assignee: ACUTUS MEDICAL, INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/735,285

(22) Filed: May 3, 2022

(65) Prior Publication Data

US 2023/0048656 A1   Feb. 16, 2023

Related U.S. Application Data

(63) Continuation of application No. 15/569,185, filed as application No. PCT/US2016/032017 on May 12, 2016, now Pat. No. 11,344,366.
(Continued)

(51) Int. Cl.
*A61B 18/14* (2006.01)
*A61B 5/00* (2006.01)
(Continued)

(52) U.S. Cl.
CPC .......... *A61B 18/1492* (2013.01); *A61B 5/283* (2021.01); *A61B 8/0883* (2013.01);
(Continued)

(58) Field of Classification Search
CPC ... A61B 5/0422; A61B 5/6859; A61B 5/6858; A61B 5/6853; A61B 18/1492;
(Continued)

(56) References Cited

U.S. PATENT DOCUMENTS

| 4,173,228 A | 11/1979 | Van Steenwyk et al. |
| 4,841,977 A | 6/1989 | Griffith et al. |

(Continued)

FOREIGN PATENT DOCUMENTS

| CA | 2825736 | 5/2008 |
| CA | 2829626 | 9/2012 |

(Continued)

OTHER PUBLICATIONS

Extended European Search Report dated Oct. 18, 2017 issued in European Application No. 15768711.
(Continued)

*Primary Examiner* — Keith M Raymond
*Assistant Examiner* — Johnathan Maynard
(74) *Attorney, Agent, or Firm* — Onello & Mello, LLP

(57) ABSTRACT

A system comprises a catheter configured for delivery to a body cavity defined by surrounding tissue; a plurality of ultrasound transducers coupled to a distal end of the catheter; and an electronics module configured to selectively turn on/off each ultrasound transducer according to a predetermined activation sequence and to process signals received from each ultrasound transducer to produce at least a 2D display of the surrounding tissue. A user can selectively calculate and display various aspects of cardiac activity. The user can display Dipole Density (DDM), Charge Density (CDM), or Voltage (V-V). The shape and location of the chamber (surface), and the potentials recorded at electrodes can be displayed. The system can also change back and forth between the different display modes, and with post process-
(Continued)

ing tools, can change how various types of information is displayed. Methods are also provided.

19 Claims, 9 Drawing Sheets

Related U.S. Application Data

(60) Provisional application No. 62/160,529, filed on May 12, 2015.

(51) Int. Cl.
*A61B 5/283* (2021.01)
*A61B 5/287* (2021.01)
*A61B 8/00* (2006.01)
*A61B 8/08* (2006.01)
*A61B 8/12* (2006.01)
*A61B 18/00* (2006.01)

(52) U.S. Cl.
CPC .............. *A61B 8/12* (2013.01); *A61B 8/4494* (2013.01); *A61B 8/466* (2013.01); *A61B 8/54* (2013.01); *A61B 5/287* (2021.01); *A61B 5/6853* (2013.01); *A61B 5/6858* (2013.01); *A61B 5/6859* (2013.01); *A61B 8/445* (2013.01); *A61B 8/483* (2013.01); *A61B 2018/00351* (2013.01)

(58) Field of Classification Search
CPC . A61B 8/12; A61B 2017/00053; A61B 8/445; A61B 8/4245; A61B 6/541; A61B 5/287; A61B 34/10; A61B 2017/00243
See application file for complete search history.

(56) References Cited

U.S. PATENT DOCUMENTS

| | | | |
|---|---|---|---|
| 5,020,540 A | 6/1991 | Chamoun | |
| 5,041,973 A | 8/1991 | Lebron et al. | |
| 5,156,151 A | 10/1992 | Imran | |
| 5,293,868 A | 3/1994 | Nardella | |
| 5,482,472 A | 1/1996 | Garoni et al. | |
| 5,499,981 A | 3/1996 | Kordis | |
| 5,555,883 A | 9/1996 | Avitall | |
| 5,595,183 A | 1/1997 | Swanson et al. | |
| 5,601,084 A | 2/1997 | Sheehan et al. | |
| 5,647,367 A | 7/1997 | Lum et al. | |
| 5,662,108 A | 9/1997 | Budd et al. | |
| 5,722,402 A * | 3/1998 | Swanson ............... | A61B 5/287 606/41 |
| 5,722,416 A | 3/1998 | Swanson et al. | |
| 5,740,808 A | 4/1998 | Panescu et al. | |
| 5,749,833 A | 5/1998 | Hakki et al. | |
| 5,759,158 A | 6/1998 | Swanson | |
| 5,782,239 A | 7/1998 | Webster, Jr. | |
| 5,795,298 A | 8/1998 | Vesley et al. | |
| 5,795,299 A | 8/1998 | Eaton et al. | |
| 5,820,568 A | 10/1998 | Willis | |
| 5,830,144 A | 11/1998 | Vesely | |
| 5,846,198 A | 12/1998 | Killmann | |
| 5,876,336 A | 3/1999 | Swanson et al. | |
| 5,928,228 A | 7/1999 | Kordis et al. | |
| 5,944,022 A | 8/1999 | Nardella et al. | |
| 5,968,040 A | 10/1999 | Swanson et al. | |
| 6,014,590 A | 1/2000 | Whayne et al. | |
| 6,024,703 A | 2/2000 | Zanelli et al. | |
| 6,066,096 A | 5/2000 | Smith et al. | |
| 6,086,532 A | 7/2000 | Panescu et al. | |
| 6,107,699 A | 8/2000 | Swanson | |
| 6,115,626 A | 9/2000 | Whayne et al. | |
| 6,187,032 B1 | 2/2001 | Ohyu et al. | |
| 6,188,928 B1 | 2/2001 | Noren et al. | |
| 6,216,027 B1 | 4/2001 | Willis et al. | |
| 6,216,043 B1 | 4/2001 | Swanson et al. | |
| 6,240,307 B1 | 5/2001 | Beatty et al. | |
| 6,301,496 B1 | 10/2001 | Reisfeld | |
| 6,396,198 B1 | 5/2002 | Okimura et al. | |
| 6,400,981 B1 | 6/2002 | Govari | |
| 6,490,474 B1 | 12/2002 | Willis et al. | |
| 6,514,249 B1 | 2/2003 | Maguire et al. | |
| 6,556,695 B1 | 4/2003 | Packer et al. | |
| 6,574,492 B1 | 6/2003 | Ben-Haim et al. | |
| 6,640,119 B1 | 10/2003 | Budd et al. | |
| 6,695,785 B2 | 2/2004 | Brisken et al. | |
| 6,716,166 B2 | 4/2004 | Govari | |
| 6,728,562 B1 | 4/2004 | Budd et al. | |
| 6,772,004 B2 | 8/2004 | Rudy | |
| 6,773,402 B2 | 8/2004 | Govari et al. | |
| 6,824,515 B2 | 11/2004 | Suorsa et al. | |
| 6,826,420 B1 | 11/2004 | Beatty et al. | |
| 6,826,421 B1 | 11/2004 | Beatty et al. | |
| 6,839,588 B1 | 1/2005 | Rudy | |
| 6,895,267 B2 | 5/2005 | Panescu et al. | |
| 6,939,309 B1 | 9/2005 | Beatty et al. | |
| 6,950,689 B1 | 9/2005 | Willis et al. | |
| 6,970,733 B2 | 11/2005 | Willis et al. | |
| 6,978,168 B2 | 12/2005 | Beatty et al. | |
| 6,990,370 B1 | 1/2006 | Beatty et al. | |
| 7,187,964 B2 | 3/2007 | Khoury | |
| 7,187,973 B2 | 3/2007 | Hauck | |
| 7,258,674 B2 | 8/2007 | Hillstead et al. | |
| 7,263,397 B2 | 8/2007 | Hauck et al. | |
| 7,285,094 B2 | 10/2007 | Nohara et al. | |
| 7,285,119 B2 | 10/2007 | Stewart et al. | |
| 7,289,843 B2 | 10/2007 | Beatty et al. | |
| 7,291,146 B2 | 11/2007 | Steinke et al. | |
| 7,351,914 B2 | 4/2008 | Kaneto et al. | |
| 7,479,141 B2 | 1/2009 | Kleen et al. | |
| 7,505,810 B2 | 3/2009 | Harlev et al. | |
| 7,536,218 B2 | 5/2009 | Govari et al. | |
| 7,573,182 B2 | 8/2009 | Savage | |
| 7,689,261 B2 | 3/2010 | Mohr et al. | |
| 7,766,838 B2 | 8/2010 | Yagi et al. | |
| 7,841,986 B2 | 11/2010 | He et al. | |
| 7,918,793 B2 | 4/2011 | Altmann et al. | |
| 7,953,475 B2 | 5/2011 | Harlev et al. | |
| 8,103,327 B2 | 1/2012 | Harlev et al. | |
| 8,147,486 B2 | 4/2012 | Honour et al. | |
| 8,150,499 B2 | 4/2012 | Gelbart et al. | |
| 8,155,756 B2 | 4/2012 | Yang et al. | |
| 8,175,680 B2 | 5/2012 | Panescu | |
| 8,200,314 B2 | 6/2012 | Bladen et al. | |
| 8,208,998 B2 | 6/2012 | Beatty et al. | |
| 8,221,411 B2 | 7/2012 | Francischelli et al. | |
| 8,233,972 B2 | 7/2012 | Zhang | |
| 8,311,613 B2 | 11/2012 | Danehorn | |
| 8,320,711 B2 | 11/2012 | Altmann et al. | |
| 8,346,339 B2 | 1/2013 | Kordis et al. | |
| 8,360,786 B2 | 1/2013 | Duryea | |
| 8,364,234 B2 | 1/2013 | Kordis et al. | |
| 8,412,307 B2 | 4/2013 | Willis et al. | |
| 8,417,313 B2 | 4/2013 | Scharf et al. | |
| 8,428,690 B2 | 4/2013 | Li et al. | |
| 8,447,377 B2 | 5/2013 | Harlev et al. | |
| 8,454,596 B2 | 6/2013 | Ma et al. | |
| 8,465,433 B2 | 6/2013 | Zwirn | |
| 8,478,388 B2 | 7/2013 | Nguyen et al. | |
| 8,512,255 B2 | 8/2013 | Scharf et al. | |
| 8,571,647 B2 | 10/2013 | Harlev et al. | |
| 8,700,119 B2 | 4/2014 | Scharf et al. | |
| 8,755,861 B2 | 6/2014 | Harlev et al. | |
| 8,825,130 B2 | 9/2014 | Just et al. | |
| 8,825,134 B2 | 9/2014 | Danehorn | |
| 8,903,510 B2 | 12/2014 | Rosenberg et al. | |
| 8,918,158 B2 | 12/2014 | Scharf et al. | |
| 8,934,988 B2 | 1/2015 | Persson et al. | |
| 8,948,837 B2 | 2/2015 | Harlev et al. | |
| 8,968,299 B2 | 3/2015 | Kauphusman et al. | |
| 8,979,839 B2 | 3/2015 | De La Rama et al. | |
| 8,989,842 B2 | 3/2015 | Li et al. | |
| 9,011,423 B2 | 4/2015 | Brewster et al. | |

(56) References Cited

U.S. PATENT DOCUMENTS

| | | | |
|---|---|---|---|
| 9,023,027 B2 | 5/2015 | Bar-Tal et al. |
| 9,026,196 B2 | 5/2015 | Curran et al. |
| 9,031,642 B2 | 5/2015 | Ghosh |
| 9,037,259 B2 | 5/2015 | Mathur |
| 9,044,245 B2 | 6/2015 | Condie et al. |
| 9,113,807 B2 | 8/2015 | Koyrakh et al. |
| 9,167,982 B2 | 10/2015 | Scharf et al. |
| 9,186,081 B2 | 11/2015 | Afonso et al. |
| 9,186,212 B2 | 11/2015 | Nabutovsky et al. |
| 9,192,318 B2 | 11/2015 | Scharf et al. |
| 9,220,425 B2 | 12/2015 | Shachar et al. |
| 9,220,432 B2 | 12/2015 | Bukhman |
| 9,241,687 B2 | 1/2016 | McGee |
| 9,351,789 B2 | 5/2016 | Novichenok et al. |
| D758,596 S | 6/2016 | Perryman et al. |
| 9,358,398 B2 | 6/2016 | Moffitt et al. |
| 9,380,953 B2 | 7/2016 | Houben et al. |
| 9,474,486 B2 | 10/2016 | Eliason et al. |
| 9,480,525 B2 | 11/2016 | Lopes et al. |
| 9,486,355 B2 | 11/2016 | Gustus et al. |
| 9,492,227 B2 | 11/2016 | Lopes et al. |
| 9,492,228 B2 | 11/2016 | Lopes et al. |
| 9,498,192 B2 | 11/2016 | Hashimshony et al. |
| 9,504,395 B2 | 11/2016 | Scharf et al. |
| 9,526,573 B2 | 12/2016 | Lopes et al. |
| 9,549,708 B2 | 1/2017 | Mercanzini et al. |
| 9,560,982 B2 | 2/2017 | Kordis et al. |
| 9,579,149 B2 | 2/2017 | Kelly et al. |
| D782,686 S | 3/2017 | Werneth et al. |
| 9,585,588 B2 | 3/2017 | Marecki et al. |
| 9,603,651 B2 | 3/2017 | Ghosh |
| 9,610,024 B2 | 4/2017 | Scharf et al. |
| 9,675,266 B2 | 6/2017 | Afonso et al. |
| 9,693,699 B2 | 7/2017 | Spector et al. |
| 9,713,730 B2 | 7/2017 | Mathur et al. |
| 9,717,555 B2 | 8/2017 | Chan et al. |
| 9,717,559 B2 | 8/2017 | Ditter et al. |
| 9,730,602 B2 | 8/2017 | Harlev et al. |
| 9,757,044 B2 | 9/2017 | Scharf et al. |
| 9,827,039 B2 | 11/2017 | Dandler et al. |
| 9,901,303 B2 | 2/2018 | Olson |
| 9,913,589 B2 | 3/2018 | Scharf et al. |
| 9,968,268 B2 | 5/2018 | Scharf et al. |
| 10,004,459 B2 | 6/2018 | Werneth et al. |
| 10,028,706 B2 | 7/2018 | Brockway et al. |
| 10,082,395 B2 | 9/2018 | Koyrakh et al. |
| 10,201,311 B2 | 2/2019 | Chou et al. |
| 10,296,707 B2 | 5/2019 | Passerini et al. |
| 10,405,828 B2 | 9/2019 | Deladi et al. |
| 10,506,948 B2 | 12/2019 | Wodlinger et al. |
| 10,593,234 B2 | 3/2020 | Zhu et al. |
| 10,653,318 B2 | 5/2020 | Welsh et al. |
| 2001/0007070 A1 | 7/2001 | Stewart et al. |
| 2002/0026118 A1 | 2/2002 | Govari |
| 2002/0045810 A1 | 4/2002 | Ben-Haim |
| 2002/0099292 A1 | 7/2002 | Brisken et al. |
| 2002/0128565 A1 | 9/2002 | Rudy |
| 2002/0165441 A1 | 11/2002 | Coleman et al. |
| 2003/0036696 A1 | 2/2003 | Willis et al. |
| 2003/0065271 A1 | 4/2003 | Khoury |
| 2003/0078494 A1 | 4/2003 | Panescu et al. |
| 2003/0120318 A1 | 6/2003 | Hauck |
| 2003/0153907 A1 | 8/2003 | Suorsa et al. |
| 2003/0158477 A1 | 8/2003 | Panescu |
| 2003/0163046 A1* | 8/2003 | Nohara ............... G01S 15/8927 600/443 |
| 2003/0176799 A1 | 9/2003 | Beatty et al. |
| 2003/0231789 A1 | 12/2003 | Willis et al. |
| 2003/0236466 A1 | 12/2003 | Tarjan et al. |
| 2004/0039312 A1 | 2/2004 | Hillstead et al. |
| 2004/0082870 A1 | 4/2004 | Rudy et al. |
| 2004/0082948 A1 | 4/2004 | Stewart et al. |
| 2004/0113498 A1 | 6/2004 | Kroenke |
| 2004/0254437 A1 | 12/2004 | Hauck et al. |
| 2005/0059880 A1 | 3/2005 | Mathias et al. |
| 2005/0101874 A1 | 5/2005 | Beatty et al. |
| 2005/0113665 A1 | 5/2005 | Mohr et al. |
| 2005/0148836 A1 | 7/2005 | Kleen et al. |
| 2005/0203375 A1* | 9/2005 | Willis ..................... A61B 5/287 600/407 |
| 2006/0052716 A1 | 3/2006 | Beatty et al. |
| 2006/0058663 A1 | 3/2006 | Willis et al. |
| 2006/0058676 A1 | 3/2006 | Yagi et al. |
| 2006/0058692 A1 | 3/2006 | Beatty et al. |
| 2006/0058693 A1 | 3/2006 | Beatty et al. |
| 2006/0084884 A1 | 4/2006 | Beatty et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0116576 A1 | 6/2006 | McGee et al. |
| 2006/0244177 A1 | 11/2006 | Kaneto et al. |
| 2007/0016007 A1 | 1/2007 | Govari et al. |
| 2007/0055150 A1 | 3/2007 | Donaldson et al. |
| 2007/0060832 A1 | 3/2007 | Levin |
| 2007/0083194 A1 | 4/2007 | Kunis et al. |
| 2007/0106146 A1 | 5/2007 | Altmann et al. |
| 2007/0167722 A1 | 7/2007 | Bladen et al. |
| 2007/0232949 A1 | 10/2007 | Saksena |
| 2008/0009758 A1 | 1/2008 | Voth |
| 2008/0146937 A1 | 6/2008 | Lee et al. |
| 2008/0287777 A1 | 11/2008 | Li et al. |
| 2008/0319297 A1 | 12/2008 | Danehorn |
| 2009/0024086 A1 | 1/2009 | Zhang et al. |
| 2009/0076483 A1 | 3/2009 | Danehorn |
| 2009/0082691 A1 | 3/2009 | Denison et al. |
| 2009/0131930 A1 | 5/2009 | Gelbart et al. |
| 2009/0143651 A1 | 6/2009 | Kallback et al. |
| 2009/0148012 A1 | 6/2009 | Altmann et al. |
| 2009/0157136 A1 | 6/2009 | Yang et al. |
| 2009/0171274 A1 | 7/2009 | Harlev et al. |
| 2009/0264781 A1 | 10/2009 | Scharf et al. |
| 2010/0023004 A1* | 1/2010 | Francischelli ..... A61B 18/1492 606/41 |
| 2010/0076426 A1 | 3/2010 | de la Rama et al. |
| 2010/0094279 A1 | 4/2010 | Kauphusman et al. |
| 2010/0168578 A1 | 7/2010 | Garson, Jr. et al. |
| 2010/0198041 A1 | 8/2010 | Christian et al. |
| 2010/0256627 A1 | 10/2010 | Ma et al. |
| 2010/0279263 A1 | 11/2010 | Duryea |
| 2010/0286551 A1 | 11/2010 | Harlev et al. |
| 2010/0298690 A1 | 11/2010 | Scharf et al. |
| 2011/0045130 A1 | 2/2011 | Edens et al. |
| 2011/0077526 A1 | 3/2011 | Zwirn |
| 2011/0092809 A1 | 4/2011 | Nguyen et al. |
| 2011/0118726 A1 | 5/2011 | De La Rama et al. |
| 2011/0125172 A1 | 5/2011 | Gelbart et al. |
| 2011/0144510 A1 | 6/2011 | Ryu et al. |
| 2011/0172658 A1 | 7/2011 | Gelbart et al. |
| 2011/0184274 A1 | 7/2011 | Rosenberg et al. |
| 2011/0201951 A1 | 8/2011 | Zhang |
| 2011/0213231 A1 | 9/2011 | Hall et al. |
| 2011/0224540 A1 | 9/2011 | Hauck et al. |
| 2011/0230775 A1 | 9/2011 | Barley et al. |
| 2011/0270237 A1 | 11/2011 | Werneth et al. |
| 2012/0078077 A1 | 3/2012 | Harlev et al. |
| 2012/0082969 A1 | 4/2012 | Schwartz et al. |
| 2012/0123296 A1 | 5/2012 | Hashimshony et al. |
| 2012/0136231 A1 | 5/2012 | Markel |
| 2012/0143298 A1 | 6/2012 | Just et al. |
| 2012/0165667 A1 | 6/2012 | Altmann et al. |
| 2012/0172702 A1 | 7/2012 | Koyrakh et al. |
| 2012/0172859 A1 | 7/2012 | Condie et al. |
| 2012/0184863 A1 | 7/2012 | Harlev et al. |
| 2012/0265054 A1 | 10/2012 | Olson |
| 2012/0271138 A1 | 10/2012 | Kordis et al. |
| 2012/0271139 A1 | 10/2012 | Kordis et al. |
| 2012/0277574 A1 | 11/2012 | Panescu |
| 2012/0302912 A1 | 11/2012 | Moffitt et al. |
| 2012/0310064 A1* | 12/2012 | McGee .................. A61B 8/12 600/373 |
| 2013/0006238 A1 | 1/2013 | Ditter et al. |
| 2013/0085361 A1 | 4/2013 | Mercanzini et al. |
| 2013/0096432 A1 | 4/2013 | Hauck |
| 2013/0158537 A1 | 6/2013 | Deladi et al. |

(56) References Cited

U.S. PATENT DOCUMENTS

| | | |
|---|---|---|
| 2013/0165916 A1 | 6/2013 | Mathur |
| 2013/0172715 A1 | 7/2013 | Just et al. |
| 2013/0190587 A1 | 7/2013 | Lopes et al. |
| 2013/0197614 A1 | 8/2013 | Gustus et al. |
| 2013/0225983 A1 | 8/2013 | Willis et al. |
| 2013/0226017 A1 | 8/2013 | Scharf et al. |
| 2013/0241929 A1 | 9/2013 | Massarwa et al. |
| 2013/0245433 A1 | 9/2013 | Deladi et al. |
| 2013/0245621 A1 | 9/2013 | Persson et al. |
| 2013/0253298 A1 | 9/2013 | Harlev et al. |
| 2013/0267853 A1 | 10/2013 | Dausch et al. |
| 2013/0274582 A1 | 10/2013 | Afonso et al. |
| 2013/0282084 A1 | 10/2013 | Mathur et al. |
| 2013/0304062 A1 | 11/2013 | Chan et al. |
| 2013/0304065 A1 | 11/2013 | Lopes et al. |
| 2013/0310827 A1 | 11/2013 | Brewster et al. |
| 2013/0330701 A1 | 12/2013 | Rubinstein et al. |
| 2014/0024910 A1 | 1/2014 | Scharf et al. |
| 2014/0081114 A1 | 3/2014 | Shachar et al. |
| 2014/0095105 A1 | 4/2014 | Koyrakh et al. |
| 2014/0121470 A1 | 5/2014 | Scharf et al. |
| 2014/0148677 A1 | 5/2014 | Liempde et al. |
| 2014/0180150 A1 | 6/2014 | Scharf et al. |
| 2014/0200429 A1 | 7/2014 | Spector et al. |
| 2014/0200489 A1 | 7/2014 | Behar et al. |
| 2014/0221803 A1 | 8/2014 | Bar-Tal et al. |
| 2014/0235988 A1 | 8/2014 | Ghosh |
| 2014/0235989 A1 | 8/2014 | Wodlinger et al. |
| 2014/0249505 A1 | 9/2014 | Bukhman |
| 2014/0257069 A1 | 9/2014 | Eliason et al. |
| 2014/0257071 A1 | 9/2014 | Curran et al. |
| 2014/0275921 A1 | 9/2014 | Harlev et al. |
| 2014/0276733 A1 | 9/2014 | VanScoy et al. |
| 2014/0276746 A1 | 9/2014 | Nabutovsky et al. |
| 2014/0276789 A1 | 9/2014 | Dandler et al. |
| 2014/0303469 A1 | 10/2014 | Kordis et al. |
| 2014/0358143 A1 | 12/2014 | Novichenok et al. |
| 2015/0038862 A1 | 2/2015 | Gijsbers et al. |
| 2015/0196217 A1 | 7/2015 | Harlev et al. |
| 2015/0196219 A1 | 7/2015 | Scharf et al. |
| 2015/0208938 A1 | 7/2015 | Houben et al. |
| 2015/0223757 A1 | 8/2015 | Werneth et al. |
| 2015/0223863 A1 | 8/2015 | Ghosh |
| 2015/0257732 A1 | 9/2015 | Ryan |
| 2015/0257825 A1 | 9/2015 | Kelly et al. |
| 2015/0294082 A1 | 10/2015 | Passerini et al. |
| 2015/0342491 A1 | 12/2015 | Marecki et al. |
| 2015/0366508 A1 | 12/2015 | Chou et al. |
| 2015/0374252 A1 | 12/2015 | de la Rama et al. |
| 2016/0007869 A1 | 1/2016 | Scharf et al. |
| 2016/0038051 A1 | 2/2016 | Scharf et al. |
| 2016/0051321 A1* | 2/2016 | Salahieh ............ A61B 1/00096 606/46 |
| 2016/0100770 A1 | 4/2016 | Afonso et al. |
| 2016/0128771 A1 | 5/2016 | Ditter et al. |
| 2016/0128772 A1 | 5/2016 | Reinders et al. |
| 2016/0192902 A1 | 7/2016 | Werneth et al. |
| 2016/0256112 A1 | 9/2016 | Brockway et al. |
| 2017/0035486 A1 | 2/2017 | Lopes et al. |
| 2017/0065204 A1 | 3/2017 | Ludwin et al. |
| 2017/0100049 A1 | 4/2017 | Scharf et al. |
| 2017/0202469 A1 | 7/2017 | Scharf et al. |
| 2017/0258347 A1 | 9/2017 | Scharf et al. |
| 2017/0311833 A1 | 11/2017 | Afonso et al. |
| 2017/0319180 A1 | 11/2017 | Henneken et al. |
| 2018/0055374 A1 | 3/2018 | Scharf et al. |
| 2018/0146948 A1 | 5/2018 | Chou et al. |
| 2018/0296114 A1 | 10/2018 | Welsh et al. |
| 2018/0315347 A1 | 11/2018 | Zhu et al. |
| 2019/0159729 A1 | 5/2019 | Chou et al. |
| 2020/0138317 A1 | 5/2020 | Scharf et al. |
| 2020/0187801 A1 | 6/2020 | Scharf et al. |
| 2021/0068694 A1 | 3/2021 | Chou et al. |

FOREIGN PATENT DOCUMENTS

| | | |
|---|---|---|
| CN | 1856213 | 11/2006 |
| CN | 101048100 | 10/2007 |
| CN | 201223445 | 4/2009 |
| CN | 201275144 | 7/2009 |
| CN | 102770085 | 11/2012 |
| CN | 104462650 | 3/2015 |
| EP | 1125549 | 8/2001 |
| EP | 1166714 | 1/2002 |
| EP | 1415608 | 10/2004 |
| EP | 1760661 | 3/2007 |
| EP | 1779787 | 5/2007 |
| EP | 2051625 | 4/2009 |
| EP | 2252203 | 11/2010 |
| EP | 2683293 | 1/2014 |
| EP | 2953550 | 8/2016 |
| JP | 08501477 | 2/1996 |
| JP | 08504333 | 5/1996 |
| JP | 08164140 | 6/1996 |
| JP | 10337207 | 5/1998 |
| JP | 11504541 | 4/1999 |
| JP | 2000510030 | 8/2000 |
| JP | 2000510250 | 8/2000 |
| JP | 2000358299 | 12/2000 |
| JP | 2001070269 | 3/2001 |
| JP | 2001522288 | 11/2001 |
| JP | 2002051998 | 2/2002 |
| JP | 2002113004 | 4/2002 |
| JP | 2002522106 | 7/2002 |
| JP | 2003509145 | 3/2003 |
| JP | 2003511098 | 3/2003 |
| JP | 2004350702 | 12/2004 |
| JP | 2005536313 | 12/2005 |
| JP | 2006071296 | 4/2006 |
| JP | 2006525072 | 11/2006 |
| JP | 2008149132 | 7/2008 |
| JP | 2009135109 | 6/2009 |
| JP | 2009136679 | 6/2009 |
| JP | 2011504363 | 2/2011 |
| JP | 2011507656 | 3/2011 |
| JP | 2012509701 | 4/2012 |
| JP | 2013188476 | 9/2013 |
| JP | 2014506171 | 3/2014 |
| JP | 2014514031 | 6/2014 |
| JP | 2014516723 | 7/2014 |
| JP | 2016511026 | 4/2016 |
| JP | 2017514553 | 6/2017 |
| WO | 9406349 | 3/1994 |
| WO | 9905971 | 2/1999 |
| WO | 0007501 | 2/2000 |
| WO | 0040166 | 7/2000 |
| WO | 0245608 | 6/2002 |
| WO | 03026722 | 4/2003 |
| WO | 2004026134 | 4/2004 |
| WO | 2006060613 | 6/2006 |
| WO | 2008014629 | 2/2008 |
| WO | 2009065042 | 5/2009 |
| WO | 2009090547 | 7/2009 |
| WO | 2011136867 | 11/2011 |
| WO | 2012068471 | 5/2012 |
| WO | 2012092016 | 7/2012 |
| WO | 2012100184 | 7/2012 |
| WO | 2012100185 | 7/2012 |
| WO | 2012110942 | 8/2012 |
| WO | 2012122517 | 9/2012 |
| WO | 2014124231 | 2/2013 |
| WO | 2013101257 | 7/2013 |
| WO | 2013123549 | 8/2013 |
| WO | 2014036439 | 3/2014 |
| WO | 20014059308 | 4/2014 |
| WO | 2014130169 | 8/2014 |
| WO | 2014137897 | 9/2014 |
| WO | 2015038607 | 3/2015 |
| WO | 2015148470 | 10/2015 |
| WO | 2016183179 | 11/2016 |
| WO | 2016183285 | 11/2016 |
| WO | 2016183468 | 11/2016 |
| WO | 2017192769 | 11/2017 |

(56) References Cited

FOREIGN PATENT DOCUMENTS

| | | |
|---|---|---|
| WO | 2017192775 | 11/2017 |
| WO | 2019144103 | 7/2019 |
| WO | 2019217430 | 11/2019 |
| WO | 2020097438 | 5/2020 |

OTHER PUBLICATIONS

Extended European Search Report dated Oct. 4, 2018 issued in corresponding European Application No. 16793503.0.
Extended European Search Report dated Sep. 29, 2014 issued in corresponding European Application No. 13176658.
International Search Report and Written Opinion dated Apr. 8, 2019, issued in corresponding International Application No. PCT/US19/14498.
International Search Report and Written Opinion dated Aug. 11, 2016 issued in corresponding International Application No. PCT/US2016/032017.
International Search Report and Written Opinion dated Aug. 18, 2016 issued in corresponding International Application No. PCT/US16/32420.
International Search Report and Written Opinion dated Aug. 4, 2017 issued in corresponding International Application No. PCT/US17/30915.
International Search Report and Written Opinion dated Aug. 8, 2016 issued in corresponding European Application No. PCT/US2016/031823.
International Search Report and Written Opinion dated Dec. 12, 2017 issued in corresponding International Application No. PCT/US2017/056064.
International Search Report and Written Opinion dated Jan. 14, 2020 issued in International Application No. PCT/US2019/060433.
International Search Report and Written Opinion dated Jul. 21, 2020 issued in corresponding International Application No. PCT/US2020/028779.
International Search Report and Written Opinion dated Jul. 23, 2019 issued in corresponding International Application No. PCT/US2019/031131.
International Search Report and Written Opinion dated Jun. 26, 2015 issued in International Application No. PCT/US2015/022187.
International Search Report and Written Opinion dated Jun. 5, 2014 issued in corresponding International Application No. PCT/US2013/057579.
International Search Report and Written Opinion dated Mar. 10, 2015 issued in corresponding International Application No. PCT/US14/54942.
International Search Report and Written Opinion dated Mar. 5, 2013 issued in corresponding International Application No. PCT/US2012/028593.
International Search Report and Written Opinion dated May 20, 2014 issued in corresponding International Application No. PCT/US14/15261.
International Search Report and Written Opinion dated Sep. 14, 2020 issued in corresponding International Application No. PCT/US2020/036110.
International Search Report and Written Opinion dated Sep. 25, 2017, issued in corresponding Application No. PCT/US17/30922.
International Search Report dated Oct. 7, 2009 issued in corresponding International Application No. PCT/IB2009/000071.
International Search Report issued Apr. 21, 2008 in related International Application No. PCT/CH2007/000380.
Invitation to Pay Additional Fees issued on Jan. 8, 2014 in corresponding International Application No. PCT/US2013/057579.
Japanese Notice of Allowance dated Feb. 27, 2018 issued in corresponding Japanese Application No. 2015-530101.
Japanese Notice of Allowance dated Jul. 11, 2017 issued in corresponding Japanese Application No. 2013-557-926, with English language summary.
Japanese Notice of Allowance dated Jul. 7, 2020 issued in corresponding Japanese Application No. 2016558799, with English translation of allowed claims.
Japanese Notice of Allowance dated Jun. 11, 2019 issued in corresponding Japanese Application No. 2018-024907, with English translation.
Japanese Notice of Allowance dated Mar. 5, 2019 issued in corresponding Japanese Application No. 2018061040, with English translation.
Japanese Notice of Allowance dated Sep. 1, 2020 issued in corresponding Japanese Application No. 2017-559320, with English summary.
Japanese Notice of Allowance dated Sep. 18, 2018 issued in corresponding Japanese Application No. 2015-557091, with English language translation.
Japanese Office Action dated Aug. 28, 2018 issued in corresponding Japanese Application No. 2016-542062, with machine translation to English.
Japanese Office Action dated Dec. 11, 2018 issued in corresponding Japanese Application No. 2018-024907, with machine translation to English.
Japanese Office Action dated Feb. 16, 2016 issued in corresponding Japanese Application No. 2013-557-926, with English language summary.
Japanese Office Action dated Feb. 19, 2019 issued in corresponding Japanese Application No. 2016-558799, with machine translation to English.
Japanese Office Action dated Jan. 31, 2017 issued in corresponding Japanese Application No. 2013-557-926, with English language summary.
Japanese Office Action dated Jan. 7, 2020 issued in corresponding Japanese Application No. 2016-558799, with machine translation to English.
Japanese Office Action dated Jul. 23, 2019 issued in corresponding Japanese Application No. 2016-542062, with machine translation to English.
Japanese Office Action dated Jul. 28, 2020 issued in corresponding Japanese Application No. 2018-195960, with machine translation to English.
Japanese Office Action dated Jun. 27, 2017 issued in corresponding Japanese Application No. 2015-530101, with English language translation.
Japanese Office Action dated Jun. 29, 2021 issued in corresponding Japanese Application No. 2020-081074, with machine translation to English.
Japanese Office Action dated Jun. 30, 2020 issued in corresponding Japanese Application No. 2017559317, with machine translation to English.
Japanese Office Action dated Mar. 10, 2020 issued in corresponding Japanese Application No. 2017-559320, with machine translation to English.
Japanese Office Action dated Mar. 17, 2020 issued in corresponding Japanese Application No. 2019-071004, with machine translation to English.
Japanese Office Action dated Nov. 2, 2021 issued in corresponding Japanese Application No. 2020-192741, with English translation.
Japanese Office Action dated Oct. 10, 2017 issued in corresponding Japanese Application No. 2015-557091, with machine translation to English.
Japanese Office Action dated Oct. 15, 2019 issued in corresponding Japanese Application No. 2018-195960, with machine translation to English.
Japanese Office Action dated Sep. 26, 2017 issued in corresponding Japanese Application No. 2017-155346, with English translation.
Summons to Attend Oral Proceedings dated Dec. 20, 2019 issued in corresponding European Application No. 13763151.1.
Della Bella et al. "Non-contact mapping to guide catheter ablation of untolerated ventrical tachycardia" European Heart Journal, May 2002, 23(9)742-752.
Flavia et al. "Wave Similarity Mapping Shows the Spatiotemporal Distribution of Fibrillatory Wave Complexity in the Human Right

(56) References Cited

OTHER PUBLICATIONS

Atrium During Paroxysmal and Chronic Atrial Fibrillation", Journal of Cardiovascular Electrophysiology, vol. 16, No. 10 (Oct. 2005) pp. 1071-1076.
Gupta et al. "Point of View Cardiac Mapping: Utility or Futility?", Indian Pacing and Electrophysiology Journal, vol. 2, No. 1, 2002, pp. 20-32.
Anatomy Warehouse, "Axis Heart Model", 2014, pp. 1-3, at http://www.anatomywarehouse.com/axis-scientific-2-part-deluxe-life-size-human-heart-a-104269. (Year: 2014).
Christoph Scharf et al. Declaration under 37 C.F.R. 1.132, Nov. 15, 2012.
Australian Examination Report dated Feb. 8, 2019 issued in corresponding Australian Application No. 2018250516.
Australian Examination Report dated Jun. 28, 2018 issued in corresponding Australian Patent Application No. 2014318872.
Australian Office Action dated Dec. 22, 2019 issued in corresponding Australian Application No. 2018278959.
Australian Office Action dated Feb. 26, 2018 issued in Australian Application No. 2017201560.
Australian Office Action dated Jan. 15, 2020 issued in corresponding Australian Application No. 2016262547.
Australian Office Action dated Jan. 26, 2019 issued in corresponding Australian Application No. 2018211348.
Australian Office Action dated Jul. 6, 2017 issued in corresponding Australian Application No. 2014214756.
Australian Office Action dated Jun. 14, 2018 issued in Australian Application No. 2014214756.
Australian Office Action dated Jun. 27, 2017 issued in corresponding Australian Application No. 2013308531.
Australian Office Action dated Mar. 16, 2020 issued in corresponding Australian Application No. 2016260522.
Australian Office Action dated Mar. 17, 2018 issued in corresponding Australian Application No. 2013308531.
Australian Office Action dated May 30, 2016 issued in related Australian Application No. 2012225250.
Australian Office Action dated Sep. 21, 2016 issued in corresponding Australian Application No. 2012225250.
Canadian Office Action dated Apr. 26, 2017 issued in corresponding Canadian Application No. 2932956.
Canadian Office Action dated Apr. 27, 2016 issued in corresponding Canadian Application No. 2747859.
Canadian Office Action dated Dec. 22, 2015 issued in corresponding Canadian Application No. 2656898.
Canadian Office Action dated Jan. 22, 2018 issued in corresponding Canadian Application No. 2932956.
Canadian Office Action dated Jul. 12, 2019 issued in the Canadian Application No. 2881457.
Canadian Office Action dated Mar. 30, 2017 issued in corresponding Canadian Application No. 2747859.
Canadian Office Action dated May 20, 2020 issued in corresponding Canadian Application No. 2881457.
Canadian Office Action dated Nov. 27, 2017 issued in corresponding Canadian Application No. 2829626.
Canadian Office Action dated Nov. 7, 2018 issued in corresponding Canadian Application No. 2932956.
Canadian Office Action dated Oct. 29, 2018 issued in corresponding Canadian Application No. 2829626.
Canadian Office Action dated Oct. 4, 2013 issued in corresponding Canadian Application No. 2659898.
Chinese Office Action dated Apr. 17, 2017 issued in corresponding Chinese Application No. 201480018328.4.
Chinese Office Action dated Apr. 8, 2020 issued in corresponding Chinese Application No. 201810153436.2.
Chinese Office Action dated Sep. 8, 2021 issued in corresponding Chinese Application No. 201680040709.1.
Communication Under Rule 71(3) EPC dated Nov. 15, 2021 issued in corresponding European Application No. 15768711.2.
Decision dated Jan. 16, 2018 issued for European Patent Application No. 09702094.5.
Decision dated Jan. 18, 2018 issued for European Patent Application No. 13176658.6.
European Office Action dated Apr. 23, 2018 issued in corresponding European Application No. 07785075.8.
European Office Action dated Apr. 28, 2014 issued in corresponding European Application No. 09702094.5.
European Office Action dated Feb. 29, 2016 issued in corresponding European Application No. 07785075.8.
European Office Action dated Feb. 6, 2019 issued in corresponding European Application No. 14843283.4.
European Office Action dated Jan. 28, 2019 issued in corresponding European Application No. 14748567.6.
European Office Action dated Jan. 31, 2018 issued in corresponding European Application No. 13763151.1.
European Office Action dated Jun. 15, 2020 issued in corresponding European Application No. 15768711.2.
European Office Action dated Mar. 21, 2017 issued in corresponding European Application No. 07785075.8.
European Office Action dated Mar. 9, 2016 issued in corresponding European Application No. 09702094.5.
European Office Action dated Mar. 9, 2016 issued in corresponding European Application No. 13176658.6.
European Office Action dated Nov. 7, 2017 issued in corresponding European Application No. 15768711.
Extended European Search Report dated Aug. 10, 2021 issued in corresponding European Application No. 19741310.7.
Extended European Search Report dated Dec. 13, 2021 issued in corresponding European Application No. 19800090.3.
Extended European Search Report dated Dec. 5, 2018 issued in corresponding European Application No. 16793622.8.
Extended European Search Report dated Jul. 23, 2021 issued in corresponding European Application No. 21150862.7.
Extended European Search Report dated Jul. 8, 2016 issued in corresponding European Application No. 14748567.6.
Extended European Search Report dated Mar. 14, 2017 issued in corresponding European Application No. 14843283.4.
Extended European Search Report dated Nov. 26, 2019 issued in corresponding European Application No. 19184148.5.
He et al. "An equivalent body surface charge model representing three-dimensional bioelectrical activity" IEEE Transactions on Biomedical Engineering, 42.7 (Jul. 7, 1995) pp. 637-646.
Jackson, JD, "Surface Distributions of Charges and Dipoles and Discontinuities in the Electric Field and Potential", Classical Electrodynamics, 3rd edition, Dec. 1998, pp. 31-34.
Leif et al., "Geometric modeling based on polygonal meshes". Eurographics 2000 Tutorial, Aug. 21, 2000.
Partial European Search Report dated Apr. 29, 2014 issued in corresponding European Application No. 13176658.
Pullan et al. "The inverse problem of electrocardiology" Northeastern University Electrical and Computer Engineering, Feb. 23, 2007.
Stevenson et al. "Recording Techniques for Clinical Electrophysiology", Journal of Cardiovascular Electrophysiology, vol. 16, No. 9, Sep. 2005, pp. 1017-1022.
Van Oosterom A: "Solidifying the solid angle." 2002 Journal of Electrocardiology 2002 vol. 35 Suppl pp. 181-192 ISSN: 0022-0736.
Wolfgang Nolting: Elektrodynamik—Grundkurs Theoretische Physik 3, Springer Spectrum, p. 89-91.

* cited by examiner

ULTRASOUND SEQUENCING METHOD

RELATED APPLICATIONS

The present application is a continuation application of U.S. patent application Ser. No. 15/569,185 filed Oct. 25, 2017, which is a 371 national stage application of Patent Cooperation Treaty Application No. PCT/US16/32017 filed May 12, 2016, entitled "Ultrasound Sequencing System And Method", which in turn claims priority under 35 USC 119(e) to U.S. Provisional Patent Application Ser. No. 62/160,529, entitled "Ultrasound Sequencing System and Method", filed May 12, 2015, which is incorporated herein by reference in its entirety.

The present application, while not claiming priority to, may be related to U.S. patent application Ser. No. 14/865,435, entitled "Method and Device for Determining and Presenting Surface Charge and Dipole Densities on Cardiac Walls", filed Sep. 25, 2015, which is a continuation of U.S. Pat. No. 9,167,982 (hereinafter the '982 patent), entitled "Method and Device for Determining and Presenting Surface Charge and Dipole Densities on Cardiac Walls", issued Oct. 27, 2015, which is a continuation of, which is a continuation of U.S. Pat. No. 8,918,158 (hereinafter the '158 patent), entitled "Method and Device for Determining and Presenting Surface Charge and Dipole Densities on Cardiac Walls", issued Dec. 23, 2014, which is a continuation of U.S. Pat. No. 8,700,119 (hereinafter the '119 patent), entitled "Method and Device for Determining and Presenting Surface Charge and Dipole Densities on Cardiac Walls", issued Apr. 15, 2014, which is a continuation of U.S. Pat. No. 8,417,313 (hereinafter the '313 patent), entitled "Method and Device for Determining and Presenting Surface Charge and Dipole Densities on Cardiac Walls", issued Apr. 9, 2013, which was a 35 USC 371 national stage filing of Patent Cooperation Treaty Application No. CH2007/000380, entitled "Method and Device for Determining and Presenting Surface Charge and Dipole Densities on Cardiac Walls", filed Aug. 3, 2007, published as WO2008/014629, which claimed priority to Swiss Patent Application No. 1251/06 filed Aug. 3, 2006, each of which is hereby incorporated by reference.

The present application, while not claiming priority to, may be related to U.S. patent application Ser. No. 14/886,449, entitled "Device and Method for the Geometric Determination of Electrical Dipole Densities on the Cardiac Wall", filed Oct. 19, 2015, which is a continuation of U.S. Pat. No. 9,192,318, entitled "Device and Method for the Geometric Determination of Electrical Dipole Densities on the Cardiac Wall", issued Nov. 24, 2015, which is a continuation of U.S. Pat. No. 8,512,255, entitled "Device and Method for the Geometric Determination of Electrical Dipole Densities on the Cardiac Wall", issued Aug. 20, 2013, published as US2010/0298690 (hereinafter the '690 publication), which was a 35 USC 371 national stage application of Patent Cooperation Treaty Application No. PCT/1609/00071 filed Jan. 16, 2009, entitled "A Device and Method for the Geometric Determination of Electrical Dipole Densities on the Cardiac Wall", published as WO2009/090547, which claimed priority to Swiss Patent Application 00068/08 filed Jan. 17, 2008, each of which is hereby incorporated by reference.

The present application, while not claiming priority to, may be related to U.S. patent application Ser. No. 14/003,671, entitled "Device and Method for the Geometric Determination of Electrical Dipole Densities on the Cardiac Wall", filed Sep. 6, 2013, which is a 35 USC 371 national stage filing of Patent Cooperation Treaty Application No. PCT/US2012/028593, entitled "Device and Method for the Geometric Determination of Electrical Dipole Densities on the Cardiac Wall", published as WO2012/122517 (hereinafter the '517 publication), which claimed priority to U.S. Patent Provisional Application Ser. No. 61/451,357, each of which is hereby incorporated by reference.

The present application, while not claiming priority to, may be related to U.S. Design application Ser. No. 29/475,273, entitled "Catheter System and Methods of Medical Uses of Same, Including Diagnostic and Treatment Uses for the Heart", filed Dec. 2, 2013, which is a 35 USC 371 national stage filing of Patent Cooperation Treaty Application No. PCT/US2013/057579, entitled "Catheter System and Methods of Medical Uses of Same, Including Diagnostic and Treatment Uses for the Heart", filed Aug. 30, 2013, which claims priority to U.S. Patent Provisional Application Ser. No. 61/695,535, entitled "System and Method for Diagnosing and Treating Heart Tissue", filed Aug. 31, 2012, which is hereby incorporated by reference.

The present application, while not claiming priority to, may be related to U.S. patent application Ser. No. 14/762,944, entitled "Expandable Catheter Assembly with Flexible Printed Circuit Board (PCB) Electrical Pathways", filed Jul. 23, 2015, which is a 35 USC 371 national stage filing of Patent Cooperation Treaty Application No. PCT/US2014/15261, entitled "Expandable Catheter Assembly with Flexible Printed Circuit Board (PCB) Electrical Pathways", filed Feb. 7, 2014, published as WO2014/124231, which claims priority to U.S. Patent Provisional Application Ser. No. 61/762,363, entitled "Expandable Catheter Assembly with Flexible Printed Circuit Board (PCB) Electrical Pathways", filed Feb. 8, 2013, which is hereby incorporated by reference.

The present application, while not claiming priority to, may be related to Patent Cooperation Treaty Application No. PCT/US2015/11312, entitled "Gas-Elimination Patient Access Device", filed Jan. 14, 2015, which claims priority to U.S. Patent Provisional Application Ser. No. 61/928,704, entitled "Gas-Elimination Patient Access Device", filed Jan. 17, 2014, which is hereby incorporated by reference.

The present application, while not claiming priority to, may be related to Patent Cooperation Treaty Application No. PCT/US2015/22187, entitled "Cardiac Analysis User Interface System and Method", filed Mar. 24, 2015, which claims priority to U.S. Patent Provisional Application Ser. No. 61/970,027, entitled "Cardiac Analysis User Interface System and Method", filed Mar. 28, 2014, which is hereby incorporated by reference.

The present application, while not claiming priority to, may be related to U.S. application Ser. No. 14/916,056, entitled "Devices and Methods for Determination of Electrical Dipole Densities on a Cardiac Surface", filed Mar. 2, 2016, which is a 35 USC 371 national stage filing of Patent Cooperation Treaty Application No. PCT/US2014/54942, entitled "Devices and Methods for Determination of Electrical Dipole Densities on a Cardiac Surface", filed Sep. 10, 2014, published as WO2015/038607, which claims priority to U.S. Patent Provisional Application Ser. No. 61/877,617, entitled "Devices and Methods for Determination of Electrical Dipole Densities on a Cardiac Surface", filed Sep. 13, 2013, which is hereby incorporated by reference.

FIELD

The present invention is generally related to systems and methods that may be useful for the diagnosis and/or treatment of cardiac arrhythmias or other cardiac diseases or disorders, such as systems, devices, and methods that may be useful in mapping cardiac activity.

BACKGROUND

For localizing the origin(s) of cardiac arrhythmias it is common practice to measure the electric potentials located on the inner surface of the heart by electrophysiological means within the patient's heart. One method is to insert electrode catheters into the heart to record cardiac potentials during normal heart rhythm or cardiac arrhythmia. If the arrhythmia has a regular activation sequence, the timing of the electric activation measured in voltage at the site of the electrode can be accumulated when moving the electrode around during the arrhythmia, to create a three-dimensional map of the electric activation. By doing this, information on the location of the source of arrhythmia(s) and mechanisms, i.e., re-entrant circuits, can be diagnosed to initiate or guide treatment (radiofrequency ablation). The information can also be used to guide the treatment of cardiac resynchronization, in which implantable pacing electrodes are placed in specific locations within the heart wall or chambers to re-establish a normal level of coordinated activation of the heart.

A method using external sensors measures the electrical activity of the heart from the body surface using electrocardiographic techniques that include, for example, electrocardiograms (ECG) and vectorcardiography (VCG). These external sensor techniques can be limited in their ability to provide information and/or data on regional electrocardiac activity. These methods can also fail to localize bioelectric events in the heart.

A method using external sensors for the localization of cardiac arrhythmias utilizes body surface mapping. In this technique, multiple electrodes are attached to the entire surface of the thorax and the information of the cardiac electrograms (surface ECG) is measured in voltages that are accumulated into maps of cardiac activation. This measurement can be problematic because the electrical activity is time dependent and spatially distributed throughout the myocardium and also fails to localize bioelectric events in the heart. Complex mathematical methods are required to determine the electrical activation upon the outer surface of a heart model (i.e. epicardium), for instance, one obtained from CT or MRI imaging giving information on cardiac size and orientation within the thoracic cavity.

Alternatively, recordings of potentials at locations on the torso, for example, can provide body surface potential maps (BSPMs) over the torso surface. Although the BSPMs can indicate regional cardiac electrical activity in a manner that can be different from conventional ECG techniques, these BSPM techniques generally provide a comparatively low resolution, smoothed projection of cardiac electrical activity that does not facilitate visual detection or identification of cardiac event locations (e.g., sites of initiation of cardiac arrhythmias) and details of regional activity (e.g., number and location of arrythmogenic foci in the heart).

Since the localization of cardiac arrhythmias by the use of potentials is imprecise, the successful treatment of cardiac arrhythmias has been difficult and has demonstrated limited success and reliability. There is, therefore, a need for improved methods of localizing, diagnosing and treating cardiac arrhythmias.

SUMMARY

In accordance with one aspect of the inventive concept, provided is a body cavity imaging system, comprising: a catheter configured for delivery to a body cavity defined by surrounding tissue; a plurality of ultrasound transducers coupled to a distal end of the catheter; an electronics module configured to selectively turn on/off each ultrasound transducer according to a predetermined activation sequence and to process signals received from each ultrasound transducer to produce at least a 2D display of the surrounding tissue.

In various embodiments, the imaging system can be part of an electrophysiology system.

In various embodiments, the cavity can be a heart chamber and the surrounding tissue can be one or more walls of the heart chamber.

In various embodiments, the display can be a 3D display of the surrounding tissue.

In various embodiments, the 3D display of the surrounding tissue can be presented on a user interface system having a display screen and user control mechanism enabling graphical manipulation of the 3D display of the surrounding tissue.

In various embodiments, the graphical manipulation can include one or more of zoom in/out, rotate, select portions or subsections of the surrounding tissue.

In various embodiments, the plurality of ultrasound transducers can be coupled to a 3D array.

In various embodiments, the 3D array can be a basket array, spiral array, a balloon, radially deployable arms, and/or other expandable and compactible structures.

In various embodiments, the ultrasound transducers can be disposed on a plurality of splines of the 3D array.

In various embodiments, the 3D array can include at least three splines.

In various embodiments, at least two ultrasound transducers can be disposed on each spline.

In various embodiments, the system can further comprise a plurality of biopotential electrodes coupled to a distal end of the catheter.

In various embodiments, the biopotential electrodes can also be disposed on a plurality of splines of the 3D array.

In various embodiments, at least some of the biopotential electrodes and at least some of the ultrasound transducers can be disposed on the same splines.

In various embodiments, a biopotential electrode and an ultrasound transducer are disposed together to form an electrode/transducer pair, and the system includes a plurality of electrode/transducer pairs.

In various embodiments, one or more splines can comprise at least one electrode/transducer pair.

In various embodiments, one or more splines can comprise a plurality of electrode/transducer pairs.

In various embodiments, a plurality of splines can comprise at least one electrode/transducer pair.

In various embodiments, a plurality of splines can comprise a plurality of electrode/transducer pairs.

In various embodiments, a plurality of splines can comprise at least three electrode/transducer pairs.

In various embodiments, each spline can comprise a flexible PCB, and each electrode/transducer pair is electrically coupled to the flexible PCB.

In various embodiments, each electrode/transducer pair can share a common communication path on the flexible PCB.

In various embodiments, all electrode/transducer pairs on a spline can share a common communication path on the flexible PCB.

In various embodiments, the common communication path can be a common ground.

In various embodiments, the system can be further configured to correlate cardiac or other electrical activity to one or more images generated using imaging device.

In various embodiments, the imaging device can comprise an imaging device selected from the group consisting of: a fluoroscope; an MRI; a CT Scanner; an ultrasound imaging device; and combinations of two or more of these.

In various embodiments, the activation sequence can be a pattern of turning on/off the plurality of ultrasound transducers that avoids the sequential activation of two neighboring ultrasound transducers.

In various embodiments, the activation sequence can avoid the sequential activation of two transducers within two or three neighboring spaces of each other.

In various embodiments, the neighboring spaces can be considered spaces on a single spline; across splines, such as transducer 1 of spline 1 and transducer 1 of spline 2; and/or diagonally across splines, such as transducer 1 of spline 1 and transducer 2 of spline 2.

In various embodiments, the activation sequence pattern can be a pattern that avoids sequential activation of two transducers from a single spline.

In accordance with another aspect of the inventive concept, provided is a method of performing a diagnostic assessment, comprising: providing a cardiac diagnostic system, including a plurality of ultrasound transducers and a plurality of electrodes coupled to the end of a diagnostic catheter; inserting the diagnostic catheter into a heart chamber of a patient; placing the cardiac diagnostic system in a diagnostic mode; performing a biopotential measurement process; performing a localization process; performing an ultrasound measurement process; and interleaving a localization process and the ultrasound process.

In various embodiments, frequencies of the ultrasound transducers do not interfere with biopotential signals and biopotential signals do not interfere with localization signals.

In various embodiments, the biopotential measurement process can be performed continuously.

In various embodiments, the biopotential measurement process can be interleaved with the localization process and the ultrasound measurement process.

In various embodiments, the method can comprise performing the localization process longer than, or multiple times for, a single ultrasound measurement process.

In various embodiments, the method can comprise performing the ultrasound measurement process longer than, or multiple times for, a single localization process.

In various embodiments, the biopotential measurement process can include measuring and analyzing biopotentials from the electrodes.

In various embodiments, the biopotential measurement process can include determining dipole densities and/or surface charge densities from the biopotential data.

In accordance with another aspect of the inventive concepts, provided is a method of performing a localization process, comprising: providing a cardiac diagnostic system, including a plurality of biopotential electrodes and, optionally, a plurality of ultrasound transducers coupled to a distal end of a catheter; inserting the diagnostic catheter into a heart chamber of a patient; placing one or more pairs of surface electrodes on the patient and defining an individual axis for each pair of electrodes; generating one or more localization signals and transmitting same to the patient through the one or more pairs of surface electrodes; recording data collected from the one or more pairs of surface electrodes; filtering the recorded data to isolate signals correlating to the generated localization signals of each pair of surface electrodes; analyzing the filtered data to determine a location of each biopotential electrode in a coordinate system relative to the patient, the coordinate system defined by the one or more pairs of surface electrodes.

In various embodiments, there can be at least two pairs of electrodes, and one individual axis can be determined for each pair of surface electrodes.

In various embodiments, there can be at least three pairs of electrodes, and one individual axis is determined for each pair of surface electrodes.

In various embodiments, the three axes can define a three axis localization system.

In various embodiments, the coordinate system can be a 3D coordinate system.

In various embodiments, an origin of the coordinate system can be logically located within the heart of the patient.

In various embodiments, the method can comprise: placing surface electrodes from a first pair on the chest and back of the patient, defining a first axis; and/or placing surface electrodes from a second pair laterally on the sides of the patient, defining a second axis; and/or placing surface electrodes from a third pair on the neck or shoulder and thigh of the patient, defining a third axis.

In various embodiments, the method can comprise: placing surface electrodes from a first pair of electrodes laterally on the sides of the patient, defining a first axis; and/or placing surface electrodes from a second pair of electrodes on the upper chest and lower back of the patient, defining a second axis; and/or placing surface electrodes from a third pair of electrodes on the upper back and lower chest of the patient, defining a third axis.

In various embodiments, each pair of surface electrodes can be individually driven with a signal having a different frequency.

In various embodiments, localization signals can be generated at a frequency in a range of about 1-100 kHz.

In various embodiments, the signals from each pair of surface electrodes can be individually recorded.

In various embodiments, the signals from each pair of surface electrodes can be individually filtered.

In various embodiments, the localization process can be interleaved with an ultrasound measurement process of the cardiac diagnostic system.

In various embodiments, the localization process can be interleaved with a biopotential measurement process of the cardiac diagnostic system.

In accordance with aspects of the inventive concept, provided is a method of performing an ultrasound measurement process, comprising: providing a cardiac diagnostic system, including a plurality of ultrasound transducers and, optionally, a plurality of biopotential electrodes coupled to a distal end of a catheter; inserting the diagnostic catheter into a heart chamber; activating (or ringing) an ultrasound transducer to generate an ultrasound transducer signal; ringing down the ultrasound transducer; sensing and recording a reflection of the ultrasound transducer signal by a source; determining a distance from the transducer to the source based on the received reflection; repeating the above steps until all ultrasound transducers have been activated; and repeating the above steps for all ultrasound transducers until the ultrasound measurement process is complete or ended.

In various embodiments, the biopotential electrodes and ultrasound transducers can be paired to form electrode/transducer pairs.

In various embodiments, the electrode/transducer pairs can be disposed on a plurality of splines of a 3D array.

In various embodiments, activating an ultrasound transducer can include closing one or more switches, thereby electrically connecting the transducer to a signal generator.

In various embodiments, the one or more switches can comprise an opto-coupler.

In various embodiments, the opto-coupler can have an activation time in a range of about 0.01 µs, or 500 µs.

In various embodiments, activating the transducer can include generating a pulsed drive signal configured to ring, vibrate, and/or otherwise cause the transducer to generate an ultrasonic pulse.

In various embodiments, the drive signal can comprise a signal with a frequency in a range of about 1 MHz and 25 MHz, such as 10 MHz.

In various embodiments, the drive signal frequency can be about 10 MHz.

In various embodiments, the drive signal can further comprise a signal with a pulse width in a range of about 0.1 µs and 10 µs.

In various embodiments, the drive signal pulse width can be about 2.0 µs.

In various embodiments, the ring down can have a duration of between about 0.05 µs and 1 µs for dissipation of vibration of the ultrasound transducer.

In various embodiments, the ring down can have a duration of about 0.1 µs.

In various embodiments, sensing the reflection can be performed for a duration in a range of about 1 µs and 200 µs.

In various embodiments, the sensing duration can be about 100 µs.

In various embodiments, the source can be an inner wall of a cardiac chamber.

In various embodiments, the activation of the transducer can cause deactivation of a paired biopotential electrode.

In various embodiments, the method can further comprise non-sequentially activating electrode/transducer pairs, thereby not broadening a temporary "blind spot" of a neighboring biopotential electrode caused by the activation of the ultrasound transducer.

In various embodiments, the patient can be a living being.

In various embodiments, the patient can be a simulated being or heart.

In accordance with aspects of the inventive concept, provided is a body cavity imaging system as shown and/or described.

In accordance with aspects of the inventive concept, provided is a cardiac diagnostic system as shown and/or described.

In accordance with aspects of the inventive concept, provided is a cardiac diagnostic process as shown and/or described.

In accordance with aspects of the inventive concept, provided is a localization process as shown and/or described.

In accordance with aspects of the inventive concept, provided is a biopotential measurement process as shown and/or described.

In accordance with aspects of the inventive concept, provided is an ultrasound imaging method as shown and/or described.

DETAILED DESCRIPTION

Figure 1:
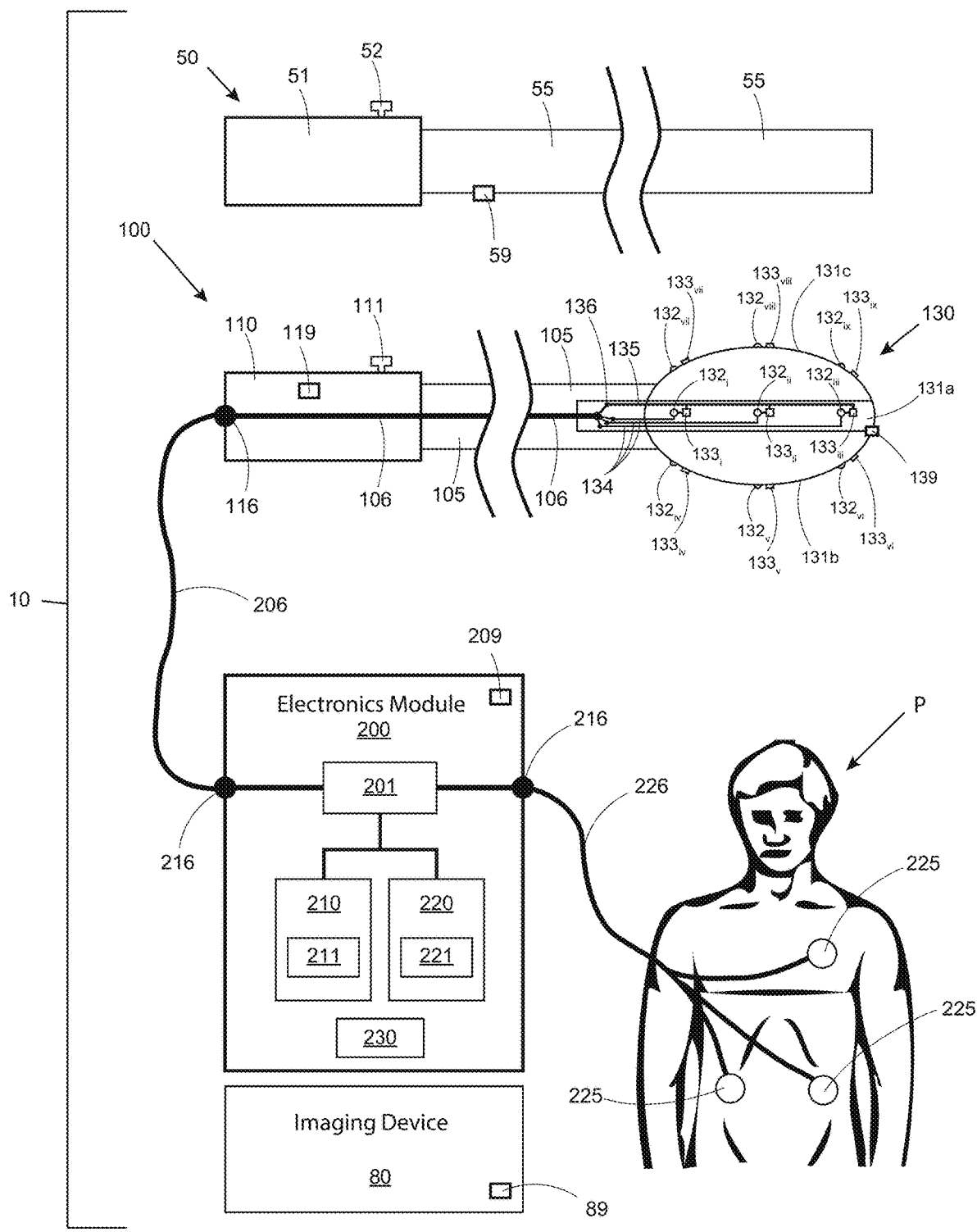
FIG. 1 illustrates a schematic view of an exemplary embodiment of a cardiac analysis system comprising a catheter with an assembly including multiple electrical components that can be deployed within a body, in accordance with aspects of the present inventive concepts.

Various exemplary embodiments will be described more fully hereinafter with reference to the accompanying drawings, in which some exemplary embodiments are shown. The present inventive concepts can, however, be embodied in many different forms and should not be construed as limited to the exemplary embodiments set forth herein.

It will be understood that, although the terms first, second, etc. are used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present invention. As used herein, the term "and/or" includes any and all combinations of one or more of the associated listed items. And a "combination" of associated listed items need not include all of the items listed, but can include all of the items listed.

It will be understood that when an element is referred to as being "on" or "attached", "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

Spatially relative terms, such as "beneath," "below," "lower," "above," "upper" and the like can be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

Various exemplary embodiments are described herein with reference illustrations of idealized or representative structures and intermediate structures. As such, variations from the shapes of the illustrations as a result, for example, of manufacturing techniques and/or tolerances, are to be expected. Thus, exemplary embodiments should not be construed as limited to the particular shapes of regions illustrated herein but are to include deviations in shapes that result, for example, from manufacturing.

To the extent that functional features, operations, and/or steps are described herein, or otherwise understood to be included within various embodiments of the present inventive concepts, such functional features, operations, and/or steps can be embodied in functional blocks, units, modules, operations and/or methods. And to the extent that such functional blocks, units, modules, operations and/or methods include computer program code, such computer program code can be stored in a computer readable medium, e.g., such as non-transitory memory and media, that is executable by at least one computer processor.

Referring now to FIG. 1, a schematic view of an embodiment of a cardiac analysis system comprising a catheter with an assembly including multiple electrical components that can be deployed within a body is illustrated, consistent with the present inventive concepts. System 10 includes diagnostic catheter 100 and electronics module 200. In some embodiments, system 10 can further include an introducer 50 and/or imaging device 80. Introducer 50 comprises handle 51 and elongate shaft 55. Shaft 55 comprises at least one lumen, such as a lumen configured to slidingly receive diagnostic catheter 100 within shaft 55. In some embodiments introducer 50 comprises a transsseptal access sheath or other device configured to provide access to a body space or cavity, such as a heart chamber, for example. Handle 51 can include a knob, lever, switch or other control, generally referred to herein as control 52. Control 52 can be configured to steer or otherwise deflect the distal end of introducer 50. Imaging device 80 can comprise an imaging device selected from the group consisting of: a fluoroscope; an MRI; a CT Scanner; an ultrasound imaging device; and combinations of two or more of these. However, other imaging devices could be used in various embodiments.

Diagnostic catheter 100 includes handle 110, and an elongate flexible shaft, shaft 105, extending from handle 110. Attached to the distal end of shaft 105 is a radially expandable and/or compactable assembly, expandable assembly 130. In an alternative embodiment, expandable assembly 130 is mounted to (e.g. surrounding) a distal portion of shaft 105, at a location proximal to the distal end of shaft 105. In some embodiments, expandable assembly 130 is constructed and arranged as described in reference to applicant's co-pending U.S. patent application Ser. No. 14/422,941, titled "System and Method for Diagnosing and Treating Heart Tissue", filed Feb. 5, 2015, the content of which is incorporated herein by reference in its entirety. Shaft 105 and expandable assembly 130 are constructed and arranged to be inserted into a body (e.g. an animal body or a human body, such as the body of Patient P), and advanced through a body vessel, such as a femoral vein, jugular vein, or other blood vessel. Shaft 105 and expandable assembly 130 can be constructed and arranged to be inserted through introducer 50, such as when expandable assembly 130 is in a compacted state, and slidingly advanced through a lumen of shaft 55 into a body space, such as a chamber of the heart, such as the right atrium or the left atrium, as examples.

Handle 110 can include one or more controls, such as control 111. Control 111 can comprise a knob, switch, lever, button, slide, or other control configured to perform a function selected from the group consisting of: steer the distal portion of shaft 105; control the expansion and/or contraction of expandable assembly 130 such as by advancing and/or retracting a control rod, not shown but such as is described herebelow in reference to FIG. 5; control the shape of expandable assembly 130, such as by advancing or retracting a control rod operably attached to expandable assembly 130; close and/or open an electrical connection, such as to provide power to one or more components of expandable assembly 130; initiate a process or otherwise send a command or other user activated signal to electronics module 200; and combinations of these.

Expandable assembly 130 can comprise a structure including multiple flexible arms or splines, splines 131a-c (singly or collectively splines 131), as shown. In some embodiments, expandable assembly 130 can comprise between two and ten splines 131, such as six splines 131. In the embodiment of FIG. 1, three splines 131a-c are equally spaced about a central axis of catheter 100 (i.e., a spacing of 120° between each spline when expandable assembly 130 is deployed in its expanded state). In other embodiments, splines 131 can be equally or unequally spaced, such as two, four, eight or twelve splines 131 with an equal spacing of 180°, 90°, 60°, 45°, and/or 30°, respectively. In some embodiments, expandable assembly 130 can comprise a balloon, radially deployable arms, and/or other expandable and compactible structure.

Expandable assembly 130 can further comprise multiple "pairs" of electrical components, for example, at least one pair comprising an electrode 132 and an ultrasound element, transducer 133. Each electrode 132 can be configured to record a voltage, such as the voltage present on a surface of the heart or at a location within a heart chamber. Each ultrasound transducer 133 can be configured to send and/or receive ultrasound signals, such as to produce an anatomical image of the tissue of at least a portion of the heart or other patient anatomical location. Electrodes 132 and ultrasound transducers 133 can comprise different shapes, such as a shape selected from the group consisting of: round; triangular; rectangular; hexagonal; trapezoidal; and combinations of two or more of these. In some embodiments, a first electrode 132 has as different shape than a second electrode 132. In some embodiments, a first ultrasound transducer 133 has a different shape than a second ultrasound transducer 133. In some embodiments, one or more ultrasound transducers 133 each comprise a single element or an array of elements (e.g. a microarray of ultrasound elements), for example an array of ultrasound elements configured as a phased array (e.g. to allow steering and/or focusing of ultrasound energy). In some embodiments, one or more ultrasound transducers 133 comprise an element selected from the group consisting of: bulk ceramic (thickness-mode or spherical); micromachined ultrasound transducer (MUT), such as piezoelectric (pMUT) or capacitive (cMUT); thin film such as PVDF; shear-wave; and combinations of two or more of these.

Each connected pair of an electrode 132 and an ultrasound transducer 133 can share a single conductor (e.g. a wire or other communication and/or power delivery conduit), such as communication path 134 (e.g. a wire) described herebelow. In some embodiments, multiple pairs of electrode 132 and ultrasound transducer 133 can collectively share a single conductor, communication path 135 (e.g. a wire), also as described herebelow.

The embodiment of FIG. 1 shows three electrode/transducer pairs per each spline 131a-c (i.e. nine pairs for expandable assembly 130), each pair comprising an electrode 132 and an ultrasound transducer 133. Spline 131a comprises three electrode/ultrasound pairs, $132_i/133_i$-$132_{iii}/133_{iii}$. Spline 131b comprises three electrode/ultrasound pairs, $132_{iv}/133_{iv}$-$132_{vi}/133_{vi}$. Spline 131c comprises three electrode/ultrasound pairs, $132_{vii}/133_{vii}$-$132_{ix}/133_{ix}$. Each electrode/ultrasound pair 132/133 is electrically or otherwise operably connected to a connection point 136 via a communication path 134, such as when splines 131 include a printed circuit (e.g. a flexible printed circuit), and communication paths 134 can comprise traces on the printed circuit, such as is described in reference to applicant's co-pending U.S. patent application Ser. No. 14/762,944, titled "Expandable Catheter Assembly with Flexible Printed Circuit Board (PCB) Electrical Pathways", filed Jul. 23, 2015, the content of which is incorporated herein by reference in its entirety. In various embodiments, such as the embodiment shown in FIG. 1, one or more electrode/ultrasound pairs 132/133 can share a common communication path 135, such as a trace configured as a common ground, electrically or otherwise operably connected to a connection point 136.

In the embodiment shown, a communication path 134 is connected to an electrode 132, such as electrode $132_i$, which is connected to the positive terminal of a paired ultrasound transducer 133, such as ultrasound transducer $133_i$. The negative terminal of ultrasound transducer $133_i$ is connected to common communication path 135. In some embodiments, two or more electrode/ultrasound pairs 132/133 can share a common communication path 135. In some embodiments, each spline 131 can comprise two or more common communication paths 135, such as a spline comprising eight electrode/ultrasound pairs 132/133, comprising two common communication paths 134, each shared by four electrode/ultrasound pairs 132/133.

A conduit comprising one or more electrical, optical, or electro-optical wires or cables (e.g. coaxial wires), such as conduit 106, can provide a communication path between one or more components of expandable assembly 130, such as one or more electrode/ultrasound pairs 132/133, and handle 110 of catheter 100. Conduit 106 terminates in handle 110 at connector 116. Connector 116 can comprise a jack, plug, terminal, port, or other custom or standard electrical, optical, or electro-optical connector. Conduit 106 can extend distally from handle 110, through one or more lumens of shaft 105, and terminate at the one or more connection points 136. In some embodiments, conduit 106 can comprise multiple coaxial cables, configured to extend through multiple lumens within shaft 105, such as when conduit 106 comprises one coaxial cable per electrode/ultrasound pair 132/133, and the coaxial shields are constructed and arranged to provide a common communication medium (e.g. a ground wire). Two or more coaxial cables can be joined to share a common communication medium, such as four or eight coaxial cables linked to create a common channel. In some embodiments, a coaxial cable can be used that comprises a gauge greater than 36AWG, such as 42AWG or 46AWG, and can comprise a nominal impedance of less than or equal to 500, and a capacitance of approximately 110 pF/m at 1 kHz.

Electronics module 200 comprises one or more connectors 216, each comprising a jack, plug, terminal, port, or other custom or standard electrical, optical, or electro-optical connector. System 10 can comprise a cable or other conduit, such as cable 206, configured to electrically, optically, and/or electro-optically connect catheter 100 to electronics module 200 via connectors 116 and 216. In some embodiments, electronics module 200 can comprise a patient isolation circuit 201, configured to electrically isolate one or more components of electronics module from Patient P (e.g. to prevent undesired delivery of a shock or other undesired electrical energy to Patient P). Isolation circuit 201 can be integral to electronics module 200 and/or it can comprise a separate discrete component (e.g. separate housing).

System 10 can further comprise one or more surface electrodes 225, e.g., such as patch electrodes configured to attach to the skin of the patient. Surface electrodes 225 are electrically connected to electronics module 200 via one or more electrical, optical or other conduits, referred to as conduits 226. Surface electrodes can be constructed and arranged to transmit and/or record signals to and/or from Patient P, such as when surface electrodes 225 transmit electrical signals to generate one or more electrical fields within Patient P, such as electrical fields used in a localization procedure as described herein. In some embodiments, system 10 can be configured to generate one or more images based upon information recorded using diagnostic catheter 100, and to correlate cardiac or other electrical activity (e.g. voltage information, dipole information and/or surface charge information) to the one or more images. Alternatively or additionally, system 10 can be configured to correlate cardiac or other electrical activity to one or more images generated using imaging device 80.

Electronics module 200 comprises electrode transceiver circuitry 210, ultrasound transceiver circuitry 220, and user interface subsystem 230. Electrode transceiver circuitry (ETC) 210 comprises one or more components selected from the group consisting of: a processor, such as a computer processor configured to perform one or more calculations based on data recoded from electrodes 132; at least one filter, such as one or more filters configured to filter one or more data sets recorded from electrodes 132; at least one signal generator, such as signal generator 211, configured to generate signals used to create a localization field as described herebelow; at least one memory module, such as a memory module configured to store data recorded from electrodes 132; and combinations of these.

Ultrasound transceiver circuitry (UTC) 220 comprises one or more components selected from the group consisting of: a processor, such as a computer processor configured to perform one or more calculations based on data recorded from ultrasound transducers 133; at least one filter, such as one or more filters configured to filter one or more data sets recorded from transducers 133; at least one signal generator, such as signal generator 221, configured to generate signals used to drive transducers 133 to cause an ultrasonic signal to be produced as described herebelow; at least one memory module, such as a memory module configured to store data recorded from transducers 133; and combinations of these. However, in some embodiments, the ETC 210 and UTC 220 can share components, such as sharing one or more processors and/or one or more memory module.

User interface subsystem 230 can comprise one or more user input and/or user output components, such as one or more components selected from the group consisting of: a keyboard; a mouse; one or more buttons or switches; a monitor; a touch screen; a speaker; a microphone; a foot pedal; a printer; a transmitter, a receiver, and combinations of these. User interface subsystem 230 can be configured to allow user input, such as to set one or more parameters associated with the operation of system 10. User interface subsystem can be further configured to display information to a user, such as information selected from the group consisting of: electrical cardiac activity information (e.g., dipole density, surface charge density, and/or voltage information, such as, voltage information measured and recorded from electrodes 132 and/or dipole or surface charge density information calculated from data recorded from electrodes 132); device localization (position) data, such as data calculated from data recorded from electrodes 132 and/or other electrodes of system 10; cardiac geometry data, such as geometry data calculated from signals provided by ultrasound transducers 133; one or more images, such as one or more images recorded from imaging device 80 and/or one or more images generated by electronics module 200 (e.g. from data provided by ultrasound transducers 133), such as a text or graphical representation of one or more calculated values by ETC 210 and/or UTC 220; and combinations of these.

In some embodiments, system 10 can comprise a system constructed and arranged to determine a dipole density map correlating to the distribution of dipole densities on the wall of a heart chamber, and/or a surface charge density map correlating to the distribution of surface charge densities on the wall of a heart chamber such as the system described in applicant's U.S. Pat. No. 8,512,255, titled "Device and Method for the Geometric Determination of Electrical Dipole Densities on the Cardiac Wall", filed Aug. 31, 2012, the content of which is incorporated herein by reference in its entirety. Alternatively or additionally, system 10 can comprise a system constructed and arranged to determine a voltage map, or other diagnostic data set of electrical or anatomic information recorded by catheter 100 and/or calculated by electronics module 200.

Electrodes 132 can be configured to record electrical activity of the heart chamber, such as by biopotentials (voltages) representing the electrical activity of the heart. Electrodes 132 can be further configured to perform a localization process, comprising recording a voltage caused by an electrical field, such as a localization field generated by surface electrodes 225. Electronics module 200 and ultrasound transducers 133 can be configured to perform an ultrasonically-based distance measurement, comprising transmitting ultrasonic signals from one or more ultrasound transducers 133, and having similar or dissimilar ultrasound transducers 133 record at least the first reflections of the transmitted signals.

ETC 210 can be configured to process data recorded by electrodes 132 to produce information selected from the group consisting of: the location of individual electrodes 132; the location, current geometry and/or orientation of expandable assembly 130 and its respective components (by processing recorded localization data); the location of one or more additional components or devices present within the heart chamber; electrical activity of a heart chamber, such as dipole density or surface charge density on the wall of the heart chamber or voltages, by processing recorded biopotential data; and combinations of these.

UTC 220 can be configured to process recorded ultrasound reflection data from ultrasound transducers 133 to produce information selected from the group consisting of: distance from a transducer 133 to a first surface of a heart chamber; distance from an ultrasound transducer 133 to a second surface of a heart chamber; distance between a first surface of a heart chamber and a second surface of a heart chamber (e.g. a heart wall thickness comprising the distance between the endocardial surface and epicardial surface of a heart chamber); location of one or more anatomic features, such as the pulmonary veins (e.g. pulmonary vein ostia); location of a cardiac valve; other anatomic geometry information; tissue velocity; tissue density; distance from a transducer 133 to a surface of another component of system 10; and combinations of these.

In some embodiments, a single component (e.g. only a single electrode 132 or a single ultrasound transducer 133) of an electrode 132/ultrasound transducer 133 pair is "activated" at a time (e.g., is provided a signal by electronics module 200 or has its signal recorded by electronics module 200). For example, during the activation period of an ultrasound transducer 133 (e.g. comprising ringing, ringing down, and/or recording), the recording and/or driving of its paired electrode 132 can be disabled (e.g. not performed or ignored). Alternatively, during the activation of an electrode 132 (e.g. driving and/or recording), driving or recording of a paired ultrasound transducer 133 can be disabled (e.g., not performed or ignored). Isolation or activation of either an electrode 132 or an ultrasound transducer 133 of a connected pair can prevent issues that can be caused by an ultrasound transducer 133 drive signal interfering with a localization drive signal (e.g. provided by a surface electrode) and/or a biopotential signal recorded by an electrode 132. In some embodiments, one or more recorded signals are filtered, allowing for simultaneous operation of ultrasound processing and biopotential processing. In some embodiments, system 10 can comprise a standard diagnostic mode, comprising performing biopotential measurements continuously, and interleaving a localization process and an ultrasound measurement process, such as process 500 described in reference to FIG. 2 herebelow. Ultrasound signals can interfere with biopotential signals, and/or biopotential signals can interfere with localization signals. In some embodiments, one or more processes (localization, ultrasound, and biopotential measurements) can be interleaved with one or more other processes, such that an individual process (or combination of processes) does not cause interference with a separate process (or combination of processes).

Figure 2:
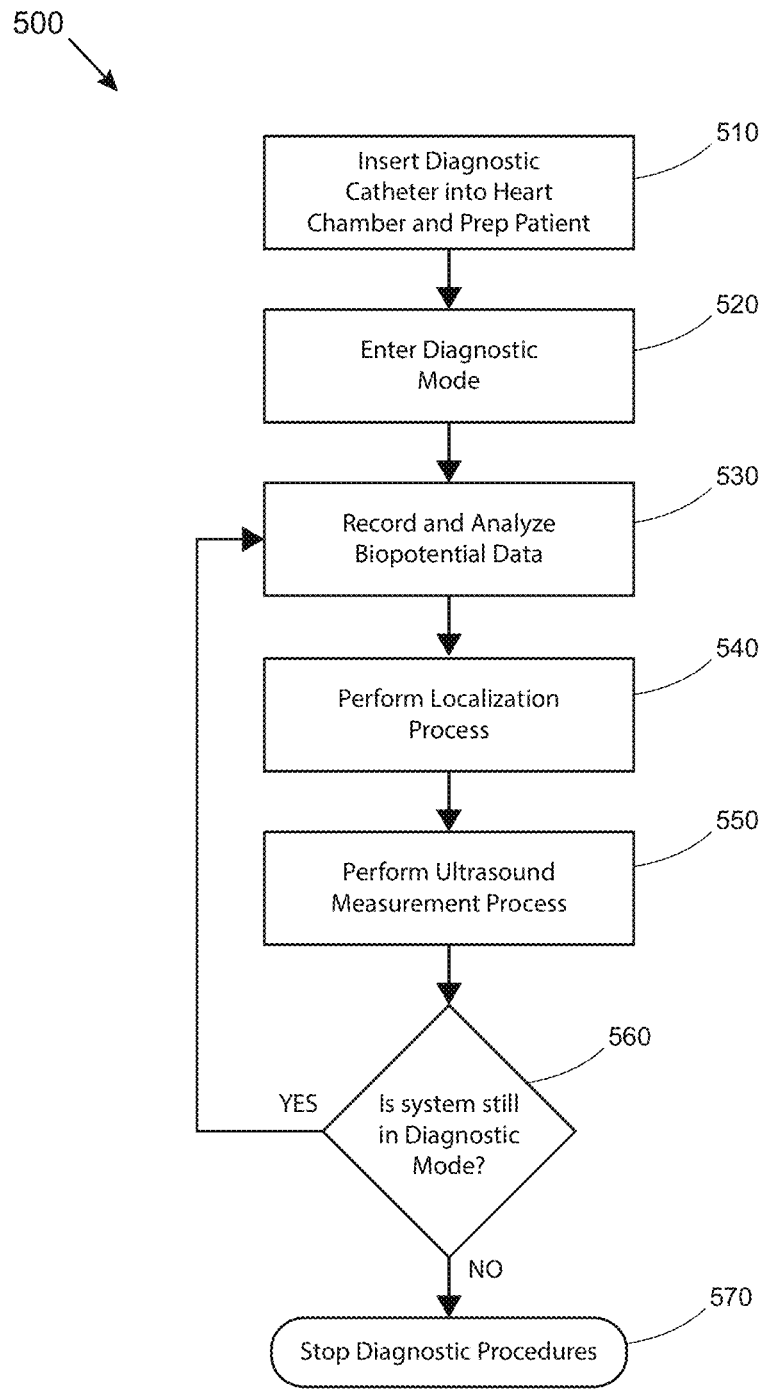
FIG. 2 provides a flowchart of an embodiment of a method of performing a diagnostic assessment, in accordance with aspects of the present inventive concepts.

During an operational mode, such as a diagnostic mode as described in FIG. 2 herebelow, the activation period of a transducer 133 causes a "blanked" period for paired electrode 132, causing a temporary "blind spot" of biopotential measurement. As described in reference to FIG. 4 herebelow, a sequencing of transducers 133 can be performed, such that the temporary "blind spot" is not extended by sequentially activating adjacent or otherwise proximate pairs 132/133.

In some embodiments, a sequence is performed as follows. During an ultrasound measurement process, all electrodes 132 can actively record biopotential signals. A first transducer $133_i$ can be activated, as described herebelow in reference to FIG. 4, causing a "blanking" of paired electrode $132_i$. Following the activation of transducer $133_i$, transducer $133_v$ can be activated, followed by $133_{ix}$, $133_{ii}$, $133_{vi}$, $133_{viii}$, $133_{iii}$, $133_{iv}$, and $133_{vii}$. In this embodiment, the "blind spot" created by the "blanking" of paired electrodes 132 follows the same pattern, moving non-sequentially about expandable assembly 130, and minimizing any potential data integrity loss due to the blind spots created.

In some embodiments, system 10 comprises one or more sensors, each configured to produce a signal, such as sensor 59 of introducer 50, a sensor of diagnostic catheter 100 (e.g. sensor 119 of handle 110 or sensor 139 of array 130), a sensor 209 of electronics module 200 and/or a sensor 89 of imaging device 80, each as shown in FIG. 1. In some embodiments, system 10 comprises two or more of sensors 59, 119, 139, 209 and/or 89. In some embodiments, sensors 59, 119, 139, 209 and/or 89 comprise a sensor selected from the group consisting of: a force sensor; a pressure sensor; a strain gauge; an optical sensor; an imaging sensor (e.g. a lens or optical fiber); a sound sensor such as an ultrasound sensor; a hall effect sensor; a pH sensor; a magnetic sensor; a temperature sensor; and combinations of one or more of these. In some embodiments, sensors 59 and/or 139 comprise a patient physiologic sensor, such as a sensor selected from the group consisting of: a blood pressure sensor; a blood gas sensor; a temperature sensor; a blood glucose sensor; a pH sensor; a respiration sensor; an average clotting time (ACT) sensor; and combinations of one or more of these. In some embodiments, system 10 is configured to analyze a signal produced by one, two or more of sensors 59, 119, 139, 209 and/or 89. In some embodiments, system 10 (e.g. electronics module 200 and/or an algorithm of ETC 210) is configured to perform an analysis of one or more signals produced by one, two or more of sensors 59, 119, 139, 209 and/or 89 in combination with voltage data, dipole density data, surface charge data, and/or anatomical data (e.g. anatomical data collected by one or more ultrasound transducers 133). In some embodiments, signals from one or more sensors 59, 119, 139, 209 and/or 89 are used by system 10 to perform a function selected from the group consisting of: improve an anatomical image displayed by system 10; improve cardiac information displayed by system 10 (e.g. dipole density and/or surface charge information); detect a malfunction of system 10; provide physiologic data of a patient; and combinations of one or more of these. In some embodiments, one or more of sensors 59, 119, 139, 209 and/or 89 can comprise a transducer (e.g. as an alternative to being a sensor or in addition to being a sensor), such as a transducer selected from the group consisting of: a heating element; a cooling element; a vibrating element; a drug or other agent delivery element; a magnetic field generating element; a light delivery element; an imaging element (such as a lens, and/or optical fiber); and combinations of one or more of these.

Referring now to FIG. 2, provided is an embodiment of a method of performing a diagnostic assessment, consistent with the present inventive concepts. In some embodiments, process 500 of FIG. 2 is accomplished using system 10 of FIG. 1 described hereabove. In STEP 510, a diagnostic catheter 100 is inserted into a heart chamber of a patient P. Further processes can be performed in order to prep the patient for a diagnostic procedure, such as a process selected from the group consisting of: applying one or more surface electrodes 225 to the patient; preparing one or more alternate imaging devices, such as imaging device 80 described hereabove; delivery of one or more drugs or other agents to the patient, such as a heart medication or blood thinner; preparing ETC 210 for use; and combinations of two or more of these.

In STEP 520, the system 10 is placed in a diagnostic mode. The diagnostic mode can be configured to produce one or more images or sets of information correlating to the anatomical shape and/or configuration of a heart chamber, and/or the electrical activity of a heart chamber, such as mapping information gathered prior to and/or during a cardiac ablation procedure. The diagnostic mode can comprise STEPS 530, 540, and 550, performed repeatedly, simultaneously, or in a particular pattern, as described herein.

In STEP 530, system 10 performs an analysis of biopotential data, determining dipole, surface charge and/or other voltage or charge based information correlating to the electrical activity of the heart, such as described in U.S. Pat. No. 8,417,313, entitled "Method and Device for Determining and Presenting Surface Charge and Dipole Densities on Cardiac Walls," which is incorporated herein by reference. Electrodes 132 are electrically connected to ETC 210 of electronics module 200 via conduits 106 and cables 206. ETC 210 can comprise one or more algorithms for determining dipole density and/or surface charge based on data recorded from electrodes 132. ETC 210 can further comprise one or more filters (e.g. hardware or software filters), configured to pass (e.g. not significantly filter) biopotential signals, while filtering other signals, specifically ultrasound and/or localization signals present within the chamber of the heart or otherwise within Patient P. In some embodiments the processes of STEP 530 can be continuously performed during the completion and/or repetition of STEPS 540 and 550, such as continuously while system 10 remains in a diagnostic mode.

In STEP 540, a localization process is performed, such as a localization process described below with reference to FIG. 3.

In STEP 550, an ultrasound measurement process is performed, such as an ultrasound measurement process described below in reference to FIG. 4.

In Step 560, if system 10 remains in a diagnostic mode, STEPS 530, 540, and 550 are repeated. In some embodiments, such as when STEP 530 is continuously performed while system 10 remains in a diagnostic mode, STEPs 540 and 550 are repeated continuously while system 10 remains in a diagnostic mode. In some embodiments STEP 540 can be performed for longer, or multiple times for a single STEP 550. In some embodiments STEP 550 can be performed for longer, or multiple times for a single STEP 540.

System 10 can be placed in an alternate mode, such as a mode selected from the group consisting of: a hold mode, such as a mode when catheter 100 remains inserted in Patient P, however diagnostic procedures are not performed; an alert mode, such as a mode when system 10 has detected an error and diagnostic and/or other procedures are halted; a shutdown/completion mode, such as a mode when system 10 is deactivated, such as to be removed from Patient P at the end of a diagnostic or treatment procedure. In STEP 560, when system 10 is determined to no longer be in a diagnostic mode, process 500 enters STEP 570. In STEP 570, all diagnostic procedures are stopped.

In some embodiments, system 10 can alternate between STEP 540 and STEP 550, such as to gather localization information and ultrasound information to generate a model of the anatomy of the heart. Subsequently, STEP 530 and STEP 540 can be performed, alternatingly or simultaneously, such as to map the electrical activity of the heart, such that system 10 can register the mapped electrical activity to the modeled anatomy gathered previously. In some embodiments, system 10 can again alternate between STEP 540 and STEP 550 to update the model of the anatomy.

Figure 3:
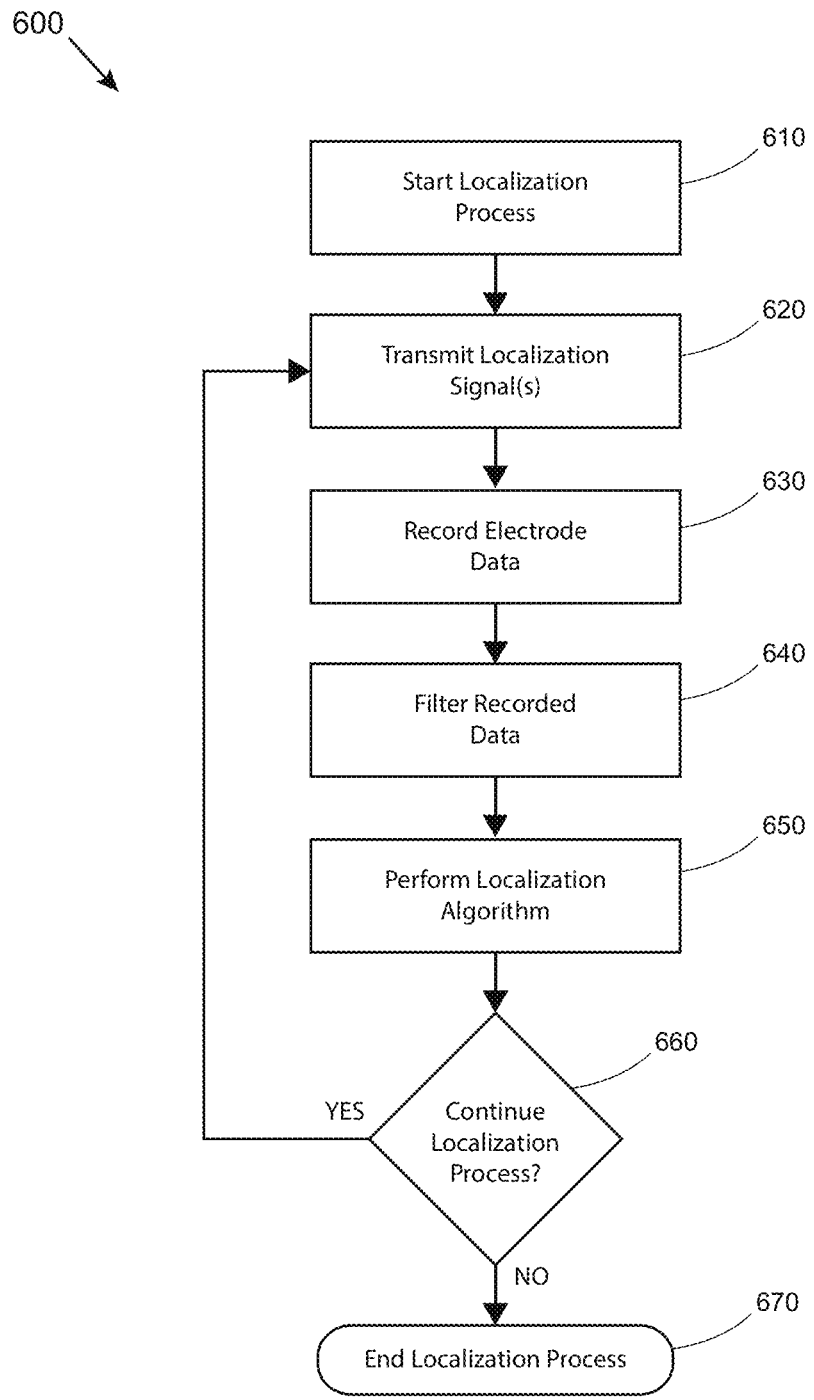
FIG. 3 provides a flowchart of an embodiment of a method of performing a localization process, in accordance with aspects of the present inventive concepts.

Referring now to FIG. 3, provided is an embodiment of a method of performing a localization process, consistent with the present inventive concepts. In some embodiments, process 600 of FIG. 3 is accomplished using system 10 of FIG. 1 described hereabove. In STEP 610, system 10 begins a localization process. In some embodiments this process can be interleaved with an ultrasound measurement process as described below with reference to FIG. 4.

In STEP 620, signal generator 211 generates one or more localization signals, transmitted to patient P through one or more surface electrodes 225 via conduits 226. Surface electrodes 225 can comprise one or more pairs of electrodes 225, such as three pairs of electrodes 225, configured to provide a three axis localization system. For example, in a three axis localization configuration, pairs of surface electrodes 225 can be placed on patient P, a first pair placed on the chest and back of patient P defining a first, X axis; a second pair placed laterally on the sides of patient P defining a second, Y axis; and a third pair placed on the neck or shoulder and thigh of patient P, defining a third, Z axis. Alternatively, a first pair of electrodes can be placed laterally on the sides of the patient defining a first axis, a second pair of electrodes can be placed on the upper chest and lower back of the patient defining a second axis, and a third pair of electrodes can be placed on the upper back and lower chest of the patient, defining a third axis. In some embodiments, signal generator 211 generates 3 or more signals of different frequencies, such as to drive three or more axes (e.g. each axis X, Y, and Z described hereabove), each at a unique frequency. The three or more axes can comprise two or more axes that are orthogonal to each other. Alternatively or additionally, signal generator 211 can generate 3 signals which differ in phase or other measurable characteristics, such that each signal (axis) can be determined via filtering to perform multi axis localization as describe herebelow. In some embodiments, each axis is powered individually (e.g. one at a time), and single axis localization can be interleaved between one or more desired axes. In the embodiment of process 600, STEP 620 can be performed continuously, throughout process 600, or throughout a diagnostic procedure (e.g. localization signals are continuously driven throughout the diagnostic procedure).

In STEP 630, ETC 210 records data collected from one or more electrodes 132, such as from each electrode 132 simultaneously or sequentially. In STEP 640, the recorded data can be filtered one or more times, such as by one or more sequential filters and/or one or more parallel filters. In an embodiment, the recorded data can be initially filtered to isolate signals correlating to the localization signals generated by generator 211, such as signals comprising a frequency between 1 and 100 kHz, such as between 10 and 100 kHz. The filtered data can subsequently be split and filtered by multiple (e.g. three) parallel filters, each configured to isolate a single frequency range, such as a frequency range associated with a single axis.

In STEP 650, the three sets of individually filtered data can be analyzed, for example by a localization algorithm, such as to determine the location of each electrode 132, in a three dimensional coordinate system relative to Patient P. In some embodiments, localization process 600 can comprise the use of more or fewer axes, such as two, three, or four axes. Additionally or alternatively, localization process 600 can comprise the use of concentric surface electrodes 225. Localization process 600 can comprise multiple filters and/or multiple data paths within ETC 210, such as multiple data paths corresponding to multiple axes, and multiple levels of data filtering.

In STEP 660, if system 10 remains in a localization process, STEPS 620 through 650 are repeated. In some embodiments system 10 can remain in a localization process for a time period between 1 µs and 1 s, such as between 50 µs and 0.5 s, such as approximately 10 ms, for example when localization process 600 is interleaved with an ultrasound measurement process and each process is performed during similar or dissimilar amounts of time. In STEP 660, when system 10 is determined to no longer be in a diagnostic mode, process 600 enters STEP 670. In STEP 670, the localization 600 process is stopped.

Figure 4:
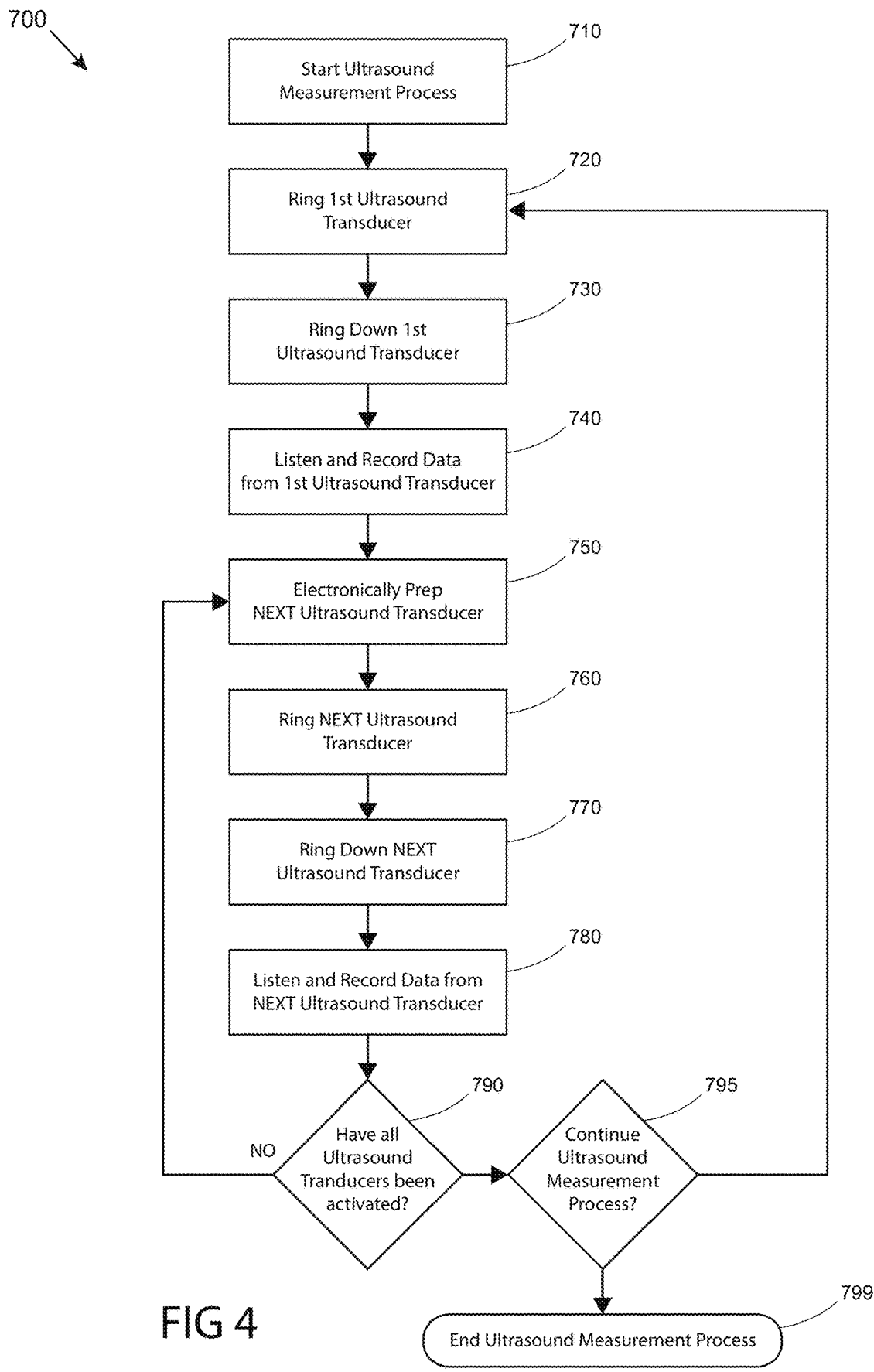
FIG. 4 provides a flowchart of an embodiment of a method of performing an ultrasound measurement process, in accordance with aspects of the present inventive concepts.

Referring now to FIG. 4, provided is a method of performing an ultrasound measurement process, consistent with the present inventive concepts. In some embodiments, process 700 of FIG. 4 is accomplished using system 10 of FIG. 1 described hereabove. In STEP 710, system 10 begins an ultrasound measurement process. In some embodiments this process can be interleaved with a localization process as described in reference to FIG. 3 hereabove.

Figure 6:
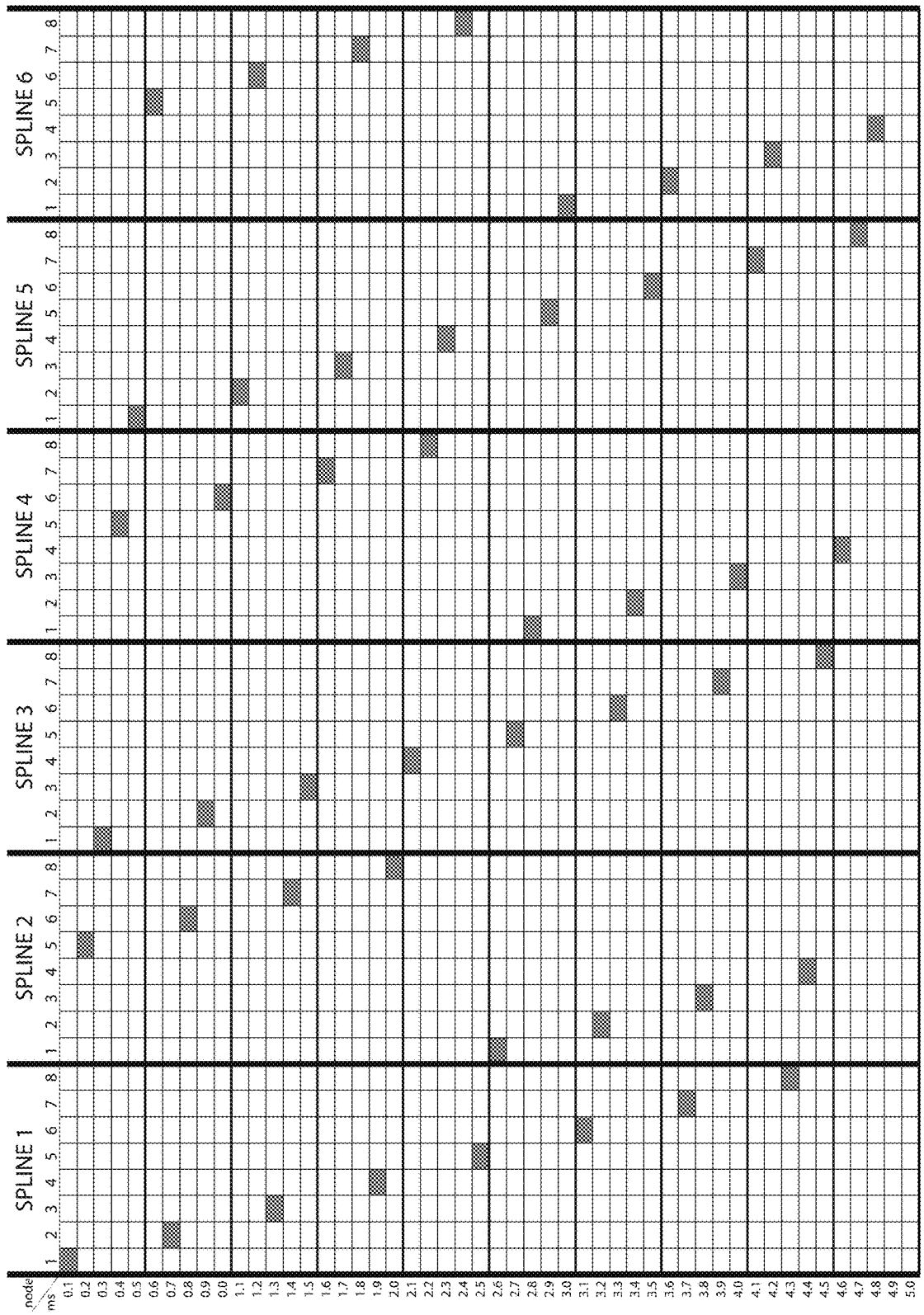
FIG. 6 provides a representation of an embodiment of an activation sequence of an array of ultrasound transducers disposed on six splines, in accordance with aspects of the present inventive concepts.

In STEP 720, UTC 220 "activates" a first transducer 133 (which can be referred to as $133_{FIRST}$), such as by closing one or more switches, electrically connecting the first transducer $133_{FIRST}$ to generator 221 and/or other electrical components of UTC 220, such as is described in reference to FIG. 6 herebelow. In some embodiments, the one or more switches can comprise an opto-coupler, such as an opto-coupler with an activation time of approximately 0.01 µs, or approximately 500 µs. Generator 221 can be configured to generate a pulsed "drive signal", configured to "ring", vibrate, and/or otherwise cause transducer 133 to generate an ultrasonic pulse. The drive signal can comprise a signal with one or more frequencies between 1 MHz and 25 MHz, such as a drive signal with at least a frequency of approximately 10 MHz. The drive signal can further comprise a signal comprising a pulse width between 0.1 µs and 10 µs, such as a pulse width of approximately 1.0 µs or 2.0 µs.

In some embodiments, such as the paired electrode/transducer embodiment of FIG. 1, the activation of a transducer 133 causes the deactivation of its paired electrode 132. During the activation period of a transducer 133, ETC 210 does not record electrical signals received by the paired electrode 132, causing a temporary "blind spot". As described herebelow, a non-sequential sequence of transducers 133 can be activated, such that the temporary "blind spot" in electrical recording is not extended by sequentially activating adjacent pairs 132/133.

In STEP 730, first transducer $133_{FIRST}$ remains activated, however is no longer being driven by generator 221. Transducer 133 "rings down" (or is "rung down"), such as to allow all driven vibration of first transducer $133_{FIRST}$ to cease and any remnant vibrations within first transducer $133_{FIRST}$ to dissipate. In some embodiments, STEP 730 can comprise a duration of between 0.05 µs and 1 µs, such as a duration of approximately 0.1 µs.

In STEP 740, UTC 220 is configured to "listen", such as by recording any ultrasonic vibrations sensed by first transducer $133_{FIRST}$, and recording reflections of one or more ultrasonic pulses generated in STEP 720. These reflections can correlate to reflections of ultrasound off of features or structures selected from the group consisting of: an inner wall of the cardiac chamber; an outer wall of the cardiac chamber; a feature of the cardiac chamber, such as a pulmonary vein or cardiac valve; a portion of a device inserted into the cardiac chamber, such as an ablation catheter and/or second mapping catheter also inserted into the cardiac chamber; and combinations of two or more of these. In some embodiments, STEP 740 can be configured to "listen" for reflections during a time period of between 1 μs and 200 μs, such as a time period of approximately 100 μs. UTC 220, or another component of electronics module 200, can be configured to determine a distance measurement, such as a measured distance from first transducer $133_{FIRST}$ to the source of the first received reflection, such as a reflection from the inner wall of the cardiac chamber. The distance measurement can be determined using techniques commonly known to those skilled in the art, such as by determining the total "travel time" of the ultrasonic pulse, and using the speed of sound in blood and/or other tissue (as appropriate) to determine the total travel distance of the pulse.

In STEP 750 a subsequent transducer, $133_{NEXT}$ can be electronically prepared. Preparation can include "activating" transducer $133_{NEXT}$, as described hereabove. STEP 750 can further comprise the deactivation of the previous transducer $133_{PREV}$, for example transducer $133_{FIRST}$. In some embodiments, activation of transducer $133_{NEXT}$ can comprise a process requiring a duration of between 0.01 μs and 500 μs, such as a duration of approximately 50 μs. In these embodiments, the activation of transducer $133_{NEXT}$ can be interleaved with a deactivation of the previous transducer $133_{PREV}$, and/or with a portion of STEP 740, such that transducer $133_{NEXT}$ is being activated while transducer $133_{PREV}$ is listening and or being deactivated. In some embodiments, these processes can overlap for a time period of between 0.01 μs and 500 μs, such as a time period of approximately 100 μs. In some embodiments, the duration from the start of an activation process of a transducer 133 to the end of a deactivation process can be between 1 μs and 700 μs, such as a duration of approximately 200 μs.

In STEPS 760 through 780, transducer $133_{NEXT}$ is rung, rung down, and listened to and recorded, as described in reference to STEPS 720 through 740 hereabove.

Figure 5:
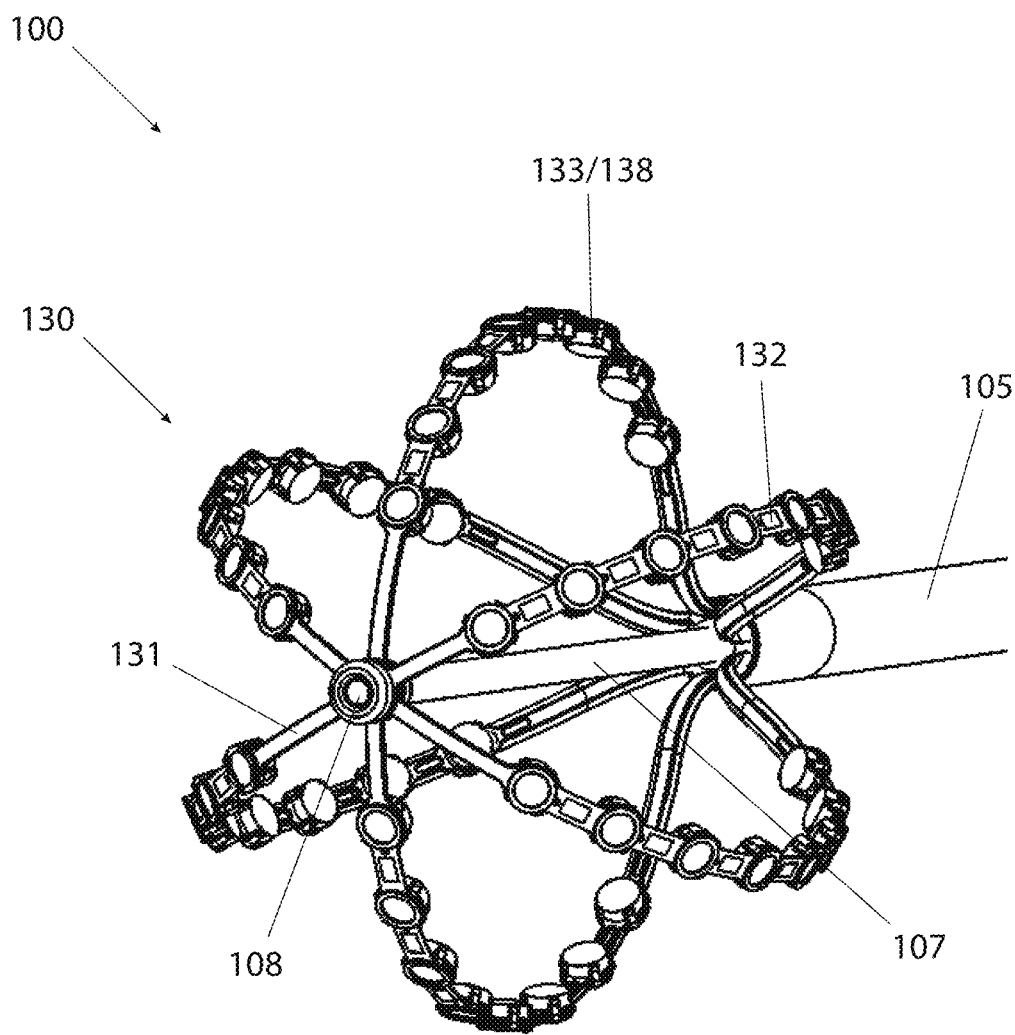
FIG. 5 provides a perspective view of an embodiment of a diagnostic catheter, in accordance with aspects of the present inventive concepts.

In STEP 790, if all transducers 133 (or a predetermined subset thereof) have not been activated since the start of process 700, STEPS 750 through 790 are repeated. In some embodiments, a subset of transducers 133 are activated per process 700, such as approximately half or approximately one third of the transducers 133, such as when two or three cycles of process 700 are required to activate all transducers 133, such as two or three cycles run sequentially or are interleaved with one or more other processes, such as process 600 of FIG. 3. In some embodiments, a complete cycle, such as a cycle in which all transducers 133 are activated, can comprise a duration of between 500 μs and 10,000 μs, such as a duration of approximately 5,000 μs. In the embodiment of FIG. 5 described herebelow, catheter 100 can comprise 48 transducers 133. Each activation period can comprise a duration of approximately 200 μs, and process 700 can comprise a duration of approximately 5 ms.

In STEP 790, if all transducers 133 (or a predetermined subset thereof) have been activated, process 700 continues to STEP 795. In STEP 795, if the measurement process is to be repeated, for example if a subsequent (similar or dissimilar) subset of transducers 133 is to be activated, STEPS 720 through 790 are repeated. If the measurement process is completed, process 700 enters STEP 799. In STEP 799, the measurement process is stopped.

Referring now to FIG. 5, provided is a perspective view of an embodiment of a diagnostic catheter that includes expandable assembly 130, consistent with the present inventive concepts. The expandable assembly 130 can be, in whole or in part, in accordance with the description of U.S. patent application Ser. No. 14/762,944, entitled "Expandable Catheter Assembly with Flexible Printed Circuit Board (PCB) Electrical Pathways", filed Jul. 23, 2015, which is incorporated herein by reference. In the embodiment of FIG. 5, the expandable assembly 130 includes a plurality of splines 131 configured as shown (i.e., six splines, radially separated by 60°, each spline comprising eight electrode transducer pairs 132/133). In this embodiment, transducers 133 are coupled to splines 131 using a housing 138. In other embodiments, multiple transducers 133 can be coupled to splines 131 (e.g. between two and twelve splines 131) in different manners.

In this embodiment, an array of transducers 133 and electrodes 132 are substantially equally distributed across splines 131, as shown in the expanded state of expandable assembly 130. Proximal ends (nearest shaft 105) of splines 131 are attached to a distal portion of shaft 105, such as at a location in and/or within shaft 105, or between shaft 105 and an inner, translatable (i.e. advanceable and retractable) shaft, control rod 107. Control rod 107 can comprise one or more conduits and/or passageways, such as lumen 108 as shown. Lumen 108 can be configured to allow for catheter 100 to be inserted over a guidewire, such as when lumen 108 is sized to slidingly receive a guidewire, and lumen 108 continues to a proximal portion of catheter 100, such as when lumen 108 exits handle 110 of catheter 100. Additionally or alternatively, lumen 108 can be sized to slidingly receive one or more devices such as a device selected from the group consisting of: an ablation catheter; a mapping catheter; a cryo ablation catheter; a tip ablation catheter; a diagnostic catheter; and combinations of two or more of these. In some embodiments, lumen 108 can be configured to allow for the delivery of one or more drugs or other agents during a diagnostic or other procedure.

In some embodiments, electrodes 132 can be positioned on the inside of splines 131. Alternatively or additionally, electrodes 132 can comprise some electrodes positioned on the inside of splines 131 and some electrodes positioned on the outside of spline 131. Alternatively or additionally, electrodes 132 can be double sided electrodes, with opposing surfaces facing both inward and outward of the basket, or electrodes 132 can comprise ring-shaped electrodes, surrounding each spline 131 respectively.

Figure 5A:
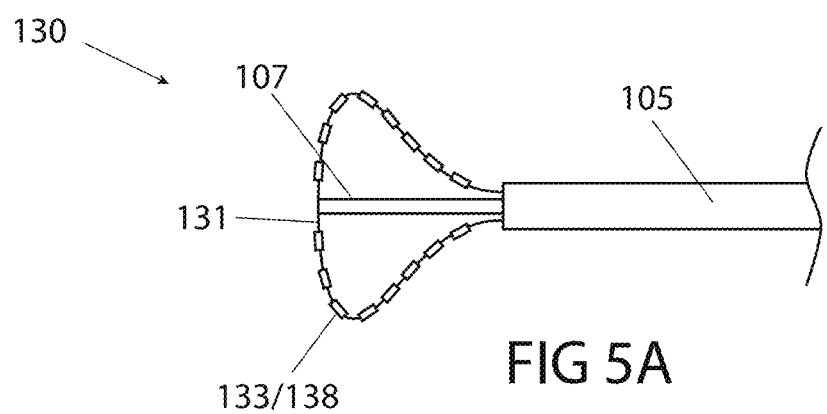
FIG. 5A is a perspective view of the catheter of FIG. 5 in an altered shape, in accordance with aspects of the present inventive concepts.

As shown, distal ends of splines 131 are connected to the distal end of control rod 107. Control rod 107 can be advanced and retracted to compact and expand, respectively, expandable assembly 130. Control rod 107 can be advanced and retracted via a control on a proximal handle, such as control 111 on handle 110 of FIG. 1. In some embodiments, control rod 107 can be retracted from a position correlating to the natural expanded position of expandable assembly 130 (as shown by example in FIG. 5), such as to deform expandable assembly 130, such as to invert a distal portion of splines 131, resulting in at least the distal most transducers 133 aligning in a forward facing direction, as shown in FIG. 5A. In this configuration, the forward facing transducers 133 can be used as an array of transducers to perform B mode scans, or other ultrasound scanning methods known in the art.

As described herein, expandable assembly 130 of FIG. 5, including forty eight electrode/transducer pairs 132/133, can be used to perform biopotential measurements, localization measurements, and/or ultrasound distance measurements. During an ultrasound measurement process, such as process 700 of FIG. 4 described hereabove, transducers 133 of expandable assembly 130 of FIG. 5 can be sequenced as described herebelow in reference to FIG. 6.

Referring now to FIG. 6, a representation of an activation sequence of an array of 48 ultrasound transducers disposed on six splines (8 per spline) is illustrated, consistent with the present inventive concepts. FIG. 6 is a particular representation of an activation sequence, representing a specific number of transducers, substantially equally spaced across a specific number of splines on an expandable assembly, such as expandable assembly 130 of FIG. 5 hereabove. Alternatively, expandable assembly 130 can have different numbers of transducers and/or splines, and a similar or dissimilar non-sequential sequence of transducer activation can be performed.

In the embodiment of FIG. 6, transducers 1-8 represent a most distal (1) transducer through a most proximal transducer (8), across each of six splines. Each activation period depicted by a solid box represents a period of activation and as described herein, a deactivation or blanking of a paired electrode. The pattern shown represents a pattern avoiding the sequential activation of two neighboring transducers, such as a pattern avoiding the sequential activation of two transducers within two or three "neighboring spaces" of each other. Neighboring spaces can be considered spaces on a single spline; across splines, such as transducer 1 of spline 1 and transducer 1 of spline 2; and/or diagonally across splines, such as transducer 1 of spline 1 and transducer 2 of spline 2. The pattern shown also represents a pattern avoiding sequential activation of two transducers from a single spline.

Figure 7:
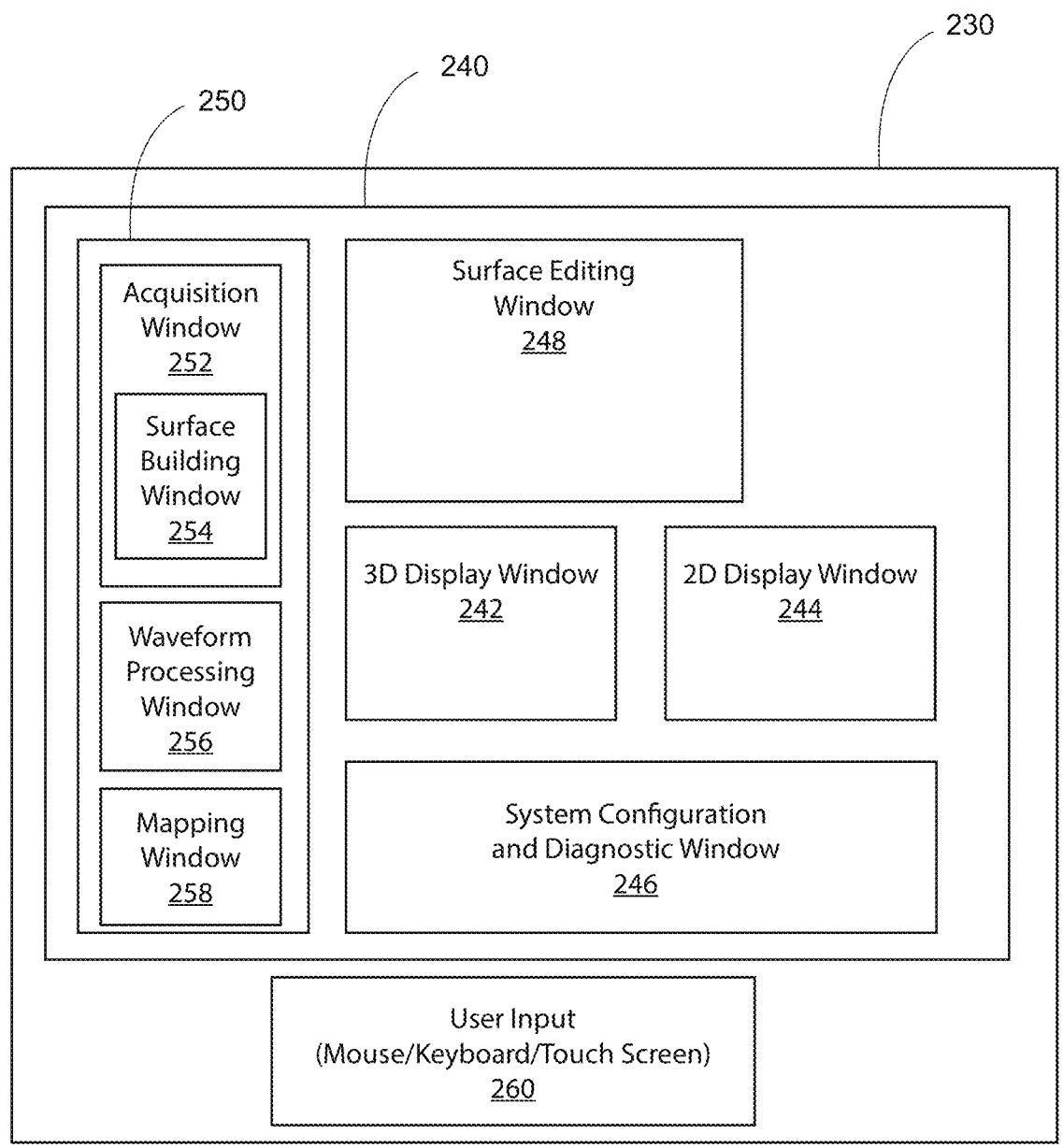
FIG. 7 provides an embodiment of a block diagram of a user interface system that can be used with a diagnostic catheter as described herein, for example, in accordance with the present inventive concepts.

FIG. 7 provides an embodiment of a block diagram of a user interface (UI) system 230 that can be used with a diagnostic catheter as described herein, for example, in accordance with the present inventive concepts.

The UI system 230 includes a display area 240, which can include one or more windows, screens, and/or monitors on which information can be rendered/shown, e.g., as 2D or 3D displays. The windows in the display area 240 need not be arranged nor relatively sized as shown in FIG. 7. And not all windows shown in display area 240 must be included. The depiction in FIG. 7 represents an illustrative embodiment, but a UI system in accordance with the inventive concept is not limited to the particular embodiment shown.

A 3D display window 242 can be included to show graphical elements in a three-dimensional (3D) space, such as a heart or heart chamber. The images and information rendered in the 3D display window 242 can change based on the user task being performed, e.g., based on the task being done in a main application window 250. The 3D display window 242 can also exist within the main application window 250, in some embodiments. The 3D display window 242 can be user interactive, and can change in response to the user interaction therewith.

A two-dimensional (2D) display window 244 can be included to show graphical elements in a two-dimensional space. The images and information rendered in the 2D window 244 can change based on the user task being performed, e.g., based on the task being done in the main application window 250. The 2D display window 244 can also exist within the main application window 250, in some embodiments. The 2D display window 244 can be user interactive, and change in response to the user interaction therewith.

The main application window 250 can include the primary workflow interface to create 3D maps. An acquisition window 252 provides tools, e.g. user interface tools, necessary to view and record biopotential signals, localization signals, and/or ultrasound signals. One tool of the acquisition window 252 allows ultrasound and localization data to be combined to reconstruct a chamber anatomy (i.e. build a digital model of a surface that represents the chamber anatomy). This representation of the anatomy can be displayed in a surface building window 254. Additionally, previously reconstructed chamber anatomies (e.g. of the patient and/or a surrogate) can be loaded from one or more data repositories, such as files, databases, or memory and displayed in the surface building window 254 to be used with live data. Configuration settings are available from this window 254 to properly register/orient a chamber reconstruction to the live data.

A waveform processing window 256 can be provided and used to allow recorded data to be reviewed, filtered, and/or analyzed. The user can use these tools to identify a time segment of data to be mapped. Segments can be from 1 sample in length to the full recorded data length. Segment selection can also take the form of passing data directly, time sample by time sample, to the mapping algorithm such that maps can be made "on the fly" (e.g. in real-time or near real-time, or pseudo real-time, "real-time" herein), without manual segment selection. The waveforms being processed can be shown in the 2D display window 244, e.g., in the form of an electrogram (EGM) or electrocardiogram (ECG or EKG). The 3D display window 242 can show any or all of the following: the voltage signals on the basket electrodes rendered onto a three-dimensional surface of the size and shape of the basket, a colored topographic surface showing the electrode signals (color and "Z-height" of the topography corresponding to voltage amplitude), with electrodes oriented in relative neighbor relationship, and/or the spatial position of the basket in relation to the reconstructed surface to show the basket position within the chamber of interest.

A mapping window 258 can be provided and used to allow configuration and execution of the mapping algorithms, including selection of a surface source model. The resulting 3D maps can be rendered in the 3D display window 242 with corresponding waveforms shown in the 2D display window 244. A time cursor or window can be included to provide a time index between display windows. The time cursor or window can be configured to slide or move across the waveforms in the 2D window in synch with a dynamically changing display rendered in the 3D window.

A system configuration and diagnostic window 246 can be provided and used to show live signals from the catheters (e.g., processed through electronics module 200)—biopotential, localization, and/or ultrasound, as examples. This window 246 can be used for verification of operation of such systems or subsystems.

A surface editing window 248 can be provided and used to allow the user to edit and process the reconstructed anatomy. Tools provided can include but are not limited to: selection (individual vertices/polygons, rectangular, elliptical, free-form shape, automatic isolated component selection and/or sharp feature selection), trimming (through-cut, front-surface cut), smoothing, re-meshing, hole-filling, subdivision, and surface deformation, such as push-pull, tools. These tools can include shape identification, component identification, isolation, extraction, appending and/or merging tools. These tools can be user interactive surface editing tools. These tools can be configured to operate manually, semi-automatically and/or automatically.

A user input module 260 can include human interface devices, such as mouse, keyboard, touchscreen, digital pen, or other devices that can be used to provide user input to and/or control of the system and its renderings.

Figure 8A:
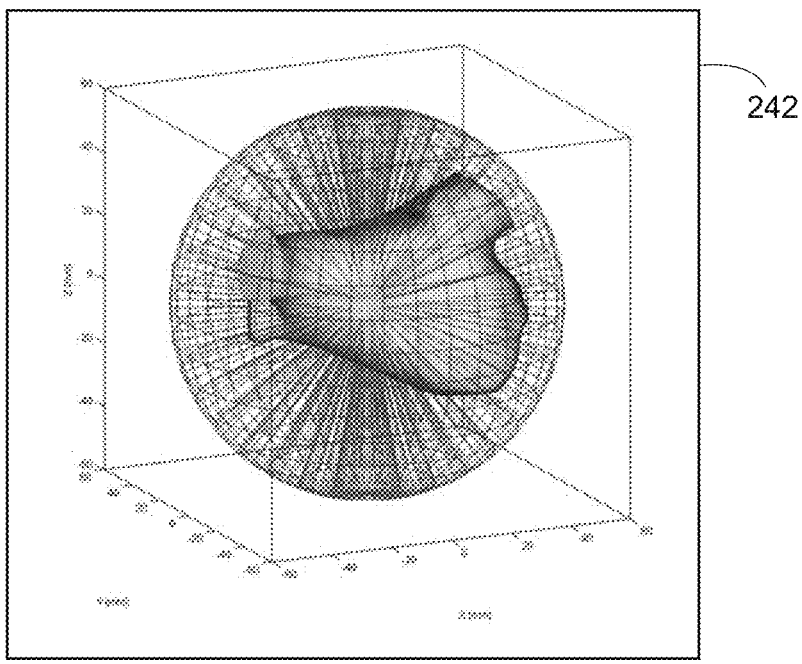
FIGS. 8A-8C provide different views relating to the output of the user interface system, in accordance with aspects of the present inventive concepts.
Figure 8C:
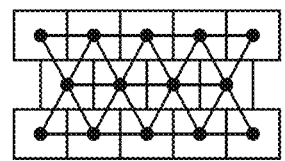
Figure 8B:
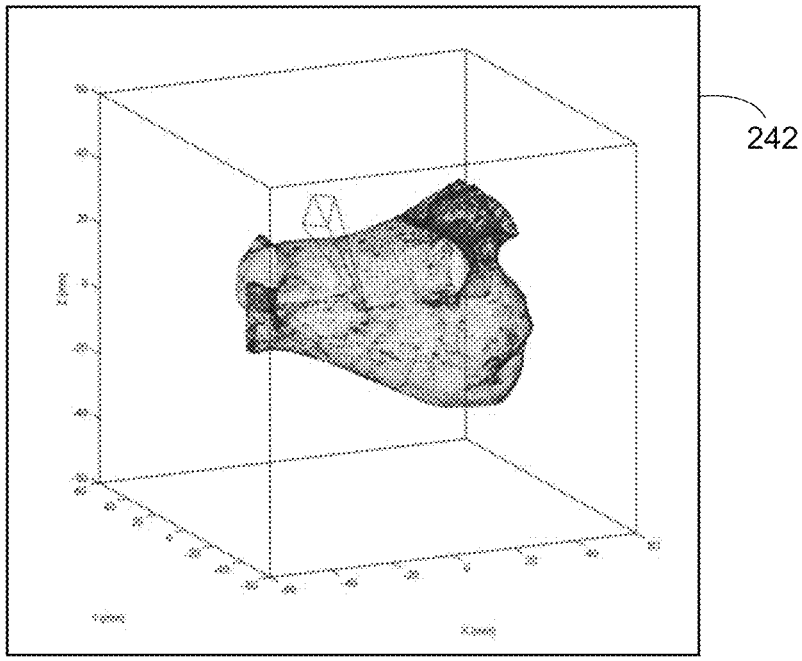

FIGS. 8A-8C provide different views relating to the output of the user interface system, in accordance with aspects of the present inventive concepts.

Referring to FIG. 8A, a point cloud (PointCloud) data structure is shown, which can be rendered in the 3D display window 242. According to this embodiment, the 3D coordinate space is divided into spherical sectors with quadrilateral cross-sections, except the poles which are N-sided. The cross-section of each bin at the same radius from the origin is configured to be similar in area. Surface point coordinates fall into one and only one bin, so do not overlap. Bin size, e.g., subtended azimuth or elevation angle, can be configurable (e.g. on instantiation). To change bin-size (and thus mesh size) and/or displacement of the surface relative to the center of the spherical bins, all surface points in an existing PointCloud can be placed into a second data structure with the desired parameters in one bulk operation.

A surface representative of the surface points in the data structure is displayed by merging all representative points or surface of each bin. In one embodiment, the representative vertices can be drawn with the interconnecting mesh between bins to form the surface. As points are added to the data structure, bins will be updated and the representative surface is updated correspondingly. Bins with no points within them can be hidden from display.

Referring to FIG. 8B, a PointCloud bin is shown and described with reference to a 3D rendering of a heart. All data points falling in each bin are analyzed to determine a representative point (vertex) or surface (surface patch) for the bin. In one embodiment, the centroid of all points in the bin is used as a representative vertex. Data within each bin can be assessed for quality, and vertices or polygons of the representative surface can be colored to indicate quality of the data. In one embodiment, the dispersion or radial distance variance in the data can indicate the detection of a cardiac valve, vein, or other radially-oriented anatomical structure.

Referring to FIG. 8C, a subset of neighboring bins are shown, and their relationships illustrated, where each bin is represented by a block. A non-manifold interconnecting mesh is calculated between neighboring bins. The orientation relationship of bins is static to avoid time-consuming recalculation of the non-manifold interconnecting mesh between neighbors.

Figure 9:
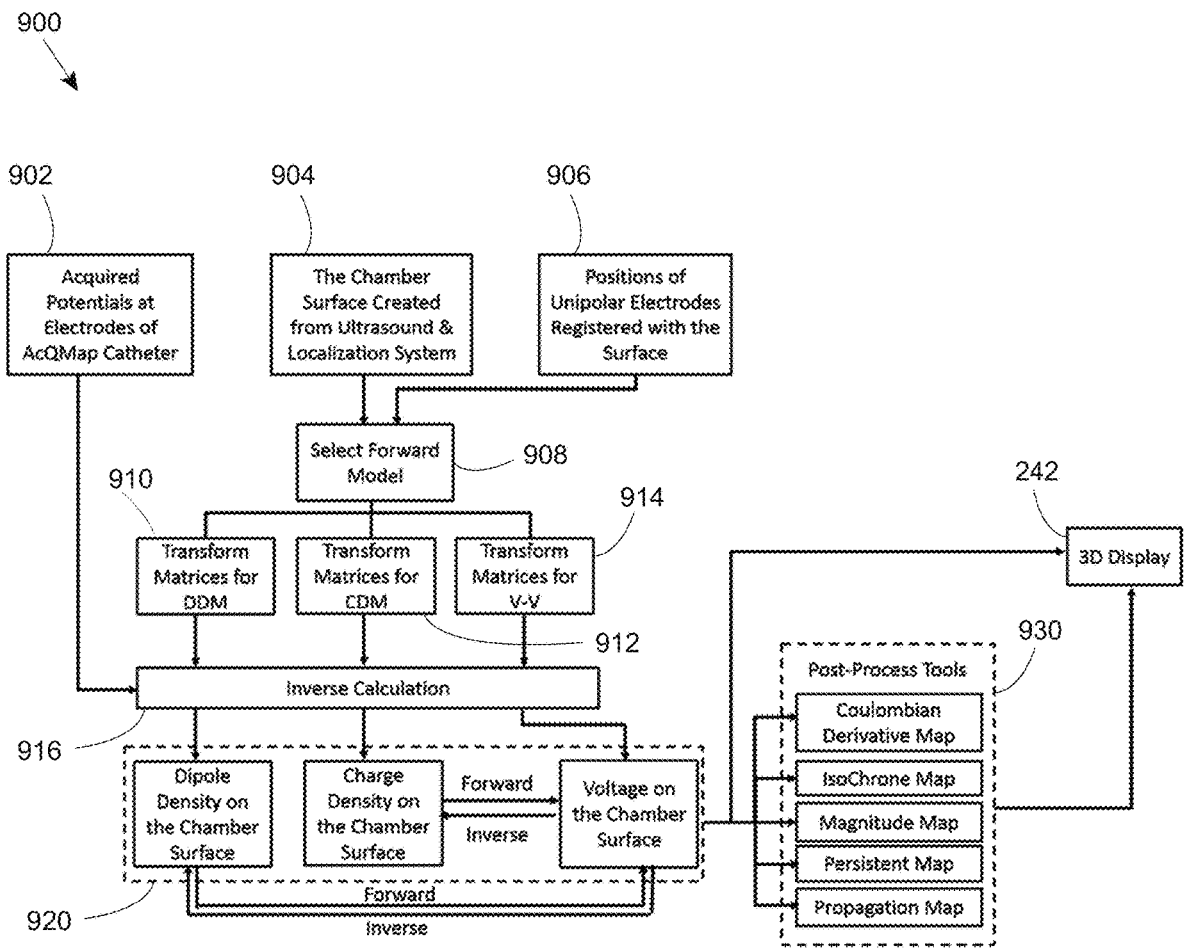
FIG. 9 provides a functional block diagram of an embodiment of a cardiac information processing system, in accordance with the present inventive concepts.

FIG. 9 provides an embodiment of a functional block diagram of a cardiac information processing system 900, in accordance with the present inventive concepts.

Using the described system from FIG. 9, a user can choose what to calculate and/or what to display, e.g., the user can display Dipole Density (DDM), Charge Density (CDM), or Voltage (V-V). This information is calculated based on information represented in the top three boxes 902, 904, 906, e.g., the position of the electrodes 902, the shape and location of the chamber (surface) 904, and the potentials recorded at the electrodes 906. The system can also be configured to support and enable changes back and forth between the different display modes, and with post processing tools, can change how that information is displayed.

The processing includes selecting a forward model 908. Based thereon, one of the following three operations can be performed: Dipole Density Mapping (DDM) 910, Charge Density Mapping (CDM) 912, and/or Voltage to Voltage Mapping (V-V) 914. In Dipole Density Mapping (DDM), electrical fields that could be measured by electrodes inside and/or outside of the heart chamber are generated from a distribution of dipole sources, having a magnitude and direction, on the surface of the heart chamber, organized and arranged as Dipole Densities (DD). In Charge Density Mapping (CDM), electrical fields that could be measured by electrodes inside or outside of the heart chamber are generated from a distribution of scalar charge sources, having a magnitude only, on the surface of the heart chamber, organized and arranged as Charge Densities (CD). And in Voltage to Voltage Mapping (V-V), no source assumption is made, and the voltages measured on electrodes inside or outside of the heart chamber are propagated from the voltages on the heart chamber surface (e.g. using Laplace's equation and/or other methods known to those skilled in electromagnetic field theory).

With the chamber surface and electrodes' positions registered with the surface as the inputs, the transform matrix, which encodes relationships between the DD/CD/Voltages on the heart chamber to the measured voltages on electrodes, is the output of the forward calculation.

An Inverse Calculation 916 is performed, with the potentials acquired from the mapping catheter and the transform matrix (the output from the forward calculation) as the inputs, the DD/CD/Voltages on the surface can be obtained by solving a linear system using a regularization method, for example the Tikhonov regularization method.

DD/CD/Voltages on the surface 920 are outputs from the inverse calculation 916. The surface voltages can be forwardly computed from the derived surface DD/CD for DDM/CDM, and surface voltages from V-V can be used to derive the surface DD/CD using the transform matrix specified by the heart chamber surface.

In some embodiments, cardiac information processing system 900 comprises post-process tool 930. Using the same, DD/CD/Voltages can be post-processed to produce a Coulombian map (an adaptation of the discrete Laplacian, or spatial second derivative of the DDM, CDM and/or Voltage maps), IsoChrone map (activation timings), Magnitude map (peak to peak magnitude or negative peak magnitude), Persistence map (active and resting status), and/or Propagation map (the wavefront), as examples.

The 3D Display 242 can be used to display the outputs from the post-processing tools 930. That is, for example, surface DD/CD/Voltages, as well as post-processing maps, can be rendered by selecting options on the display panel of UI system 230. The 3D maps can be rotated to different viewing angles and a color map can be adjusted by a user, as examples.

While the foregoing has described what are considered to be the best mode and/or other preferred embodiments, it is understood that various modifications can be made therein and that the invention or inventions may be implemented in various forms and embodiments, and that they may be applied in numerous applications, only some of which have been described herein. It is intended by the following claims to claim that which is literally described and all equivalents thereto, including all modifications and variations that fall within the scope of each claim.

We claim:

1. A method of performing an imaging process, comprising:

providing a body cavity imaging system comprising:
a catheter configured for delivery to a body cavity defined by surrounding tissue;

a plurality of ultrasound transducer/biopotential electrode pairs disposed on a plurality of splines of the 3D array; and an electronics module coupled to the catheter; and the electronics module;

selectively turning on/off each ultrasound transducer according to a predetermined activation sequence and processing signals received from each ultrasound transducer to produce a 3D display of the surrounding tissue; and the activation sequence comprising a pattern of turning on/off transducers from the plurality of ultrasound transducers over a plurality of activation periods, wherein neighboring ultrasound transducers are not sequentially activated in two consecutive activation periods on a single spline, across splines, and/or diagonally across splines.

2. The method of claim 1, wherein the body cavity is a heart chamber and the surrounding tissue is one or more walls of the heart chamber.

3. The method of claim 1, comprising presenting the 3D display of the surrounding tissue on a user interface system having a display screen and user control mechanism enabling graphical manipulation of the 3D display of the surrounding tissue.

4. The method of claim 1, wherein the 3D array is a basket array, spiral array, a balloon, radially deployable arms, and/or other expandable and compactible structures.

5. The method of claim 1, wherein the 3D array includes at least three splines.

6. The method of claim 1, wherein at least two ultrasound transducers are disposed on each spline.

7. The method of claim 1, wherein at least some of the biopotential electrodes and at least some of the ultrasound transducers are disposed on the same splines.

8. The method of claim 1, wherein one or more splines comprise a plurality of electrode/transducer pairs.

9. The method of claim 1, wherein a plurality of splines comprises at least one electrode/transducer pair.

10. The method of claim 1, wherein each spline comprises a flexible PCB, and each electrode/transducer pair is electrically coupled to the flexible PCB.

11. The method of claim 1, wherein each electrode/transducer pair shares a common communication path.

12. The method of claim 1, wherein all electrode/transducer pairs on a spline share a common communication path.

13. The method of claim 1, wherein all electrode/transducer pairs on a spline share a common ground.

14. The method of claim 1, further comprising the electronics module correlating cardiac or other electrical activity to one or more images generated using an imaging device.

15. The method of claim 14, wherein the imaging device comprises an imaging device selected from the group consisting of:
a fluoroscope; and MRI;
a CT Scanner, an ultrasound imaging device; and
combinations of two or more of these.

16. The method of claim 1, including the activation sequence avoiding sequential activation of two transducers from a single spline.

17. The method of claim 1, wherein the electronic module comprises one or more switches and the method includes the one or more switches selectively opening and/or closing to activate one or more transducers from the plurality of transducers, thereby electrically connecting the one or more transducers to a signal generator.

18. The method of claim 17, wherein the one or more switches comprises an opto-coupler.

19. The method of claim 18, wherein the opto-coupler has an activation time in a range of about 0.01 µs to 500 µs.

* * * * *

UNITED STATES PATENT AND TRADEMARK OFFICE
CERTIFICATE OF CORRECTION

| | | |
|---|---|---|
| PATENT NO. | : 12,161,398 B2 | Page 1 of 1 |
| APPLICATION NO. | : 17/735285 | |
| DATED | : December 10, 2024 | |
| INVENTOR(S) | : Derrick R. Chou et al. | |

It is certified that error appears in the above-identified patent and that said Letters Patent is hereby corrected as shown below:

In the Claims

Column 25, Line 2, Claim 1 replace the word "the" with --a--.

Column 25, Line 5, Claim 1 replace ";" with --:--.

Signed and Sealed this
Eleventh Day of February, 2025

Coke Morgan Stewart
*Acting Director of the United States Patent and Trademark Office*